United States Patent
Queval

(10) Patent No.: US 12,290,361 B2
(45) Date of Patent: May 6, 2025

(54) SAMPLE COLLECTION DEVICE, SYSTEM AND METHOD FOR EXTRACTING AND COLLECTING A SAMPLE OF A FLUID OF A USER

(71) Applicant: Loop Medical SA, Lutry (CH)

(72) Inventor: Arthur Queval, Lutry (CH)

(73) Assignee: LOOP MEDICAL SA, Lutry (CH)

( * ) Notice: Subject to any disclaimer, the term of this patent is extended or adjusted under 35 U.S.C. 154(b) by 1050 days.

(21) Appl. No.: 17/055,547

(22) PCT Filed: May 14, 2019

(86) PCT No.: PCT/IB2019/053986
§ 371 (c)(1),
(2) Date: Nov. 13, 2020

(87) PCT Pub. No.: WO2019/220340
PCT Pub. Date: Nov. 21, 2019

(65) Prior Publication Data
US 2021/0106261 A1  Apr. 15, 2021

(30) Foreign Application Priority Data
May 14, 2018 (CH) ........................................ 595/18

(51) Int. Cl.
*A61B 5/151* (2006.01)
*A61B 5/15* (2006.01)

(52) U.S. Cl.
CPC .. *A61B 5/150022* (2013.01); *A61B 5/150068* (2013.01); *A61B 5/150305* (2013.01);
(Continued)

(58) Field of Classification Search
None
See application file for complete search history.

(56) References Cited

U.S. PATENT DOCUMENTS 5,662,127 A  9/1997 De Vaughn
6,283,926 B1  9/2001 Cunningham et al.
(Continued)

FOREIGN PATENT DOCUMENTS

CN  1879016 A  12/2006
CN  201379576 Y  1/2010
(Continued)

OTHER PUBLICATIONS

ISA European Patent Office, International Search Report Issued in Application No. PCT/IB2019/053986, Aug. 6, 2019, WIPO, 3 pages.
(Continued)

*Primary Examiner* — Meredith Weare
(74) *Attorney, Agent, or Firm* — McCoy Russell LLP

(57) ABSTRACT

A system for extracting and collecting a sample of a fluid of a user, comprising a sample collection device, comprising a sample container arranged to receive said sample; a cap arranged to cooperate with the sample container and having an incision mechanism movable in the cap by a triggering mechanism; a sealing mechanism; a sample extraction device, comprising a vacuum creation mechanism arranged to create vacuum in a vacuum chamber; and a valve control mechanism arranged to release the vacuum from the vacuum chamber to the sample collection device. The system simplifies collection of a fluid (e.g., blood) sample while keeping a high-quality standard for its analysis, minimizes the risk of injury due to handling the sample, reduces the risk of contamination of the collected sample, is compatible with standard blood analysers of central laboratories, requires minimal action from the user, and can collect large volumes of bodily fluid.

20 Claims, 37 Drawing Sheets

(52) U.S. Cl.
CPC .. *A61B 5/150312* (2013.01); *A61B 5/150343* (2013.01); *A61B 5/150351* (2013.01); *A61B 5/150442* (2013.01); *A61B 5/150847* (2013.01); *A61B 5/15113* (2013.01); *A61B 5/15144* (2013.01)

(56) References Cited

U.S. PATENT DOCUMENTS

| | | |
|---|---|---|
| 9,217,229 B2 | 12/2015 | Ball |
| 2002/0087180 A1 | 7/2002 | Searle et al. |
| 2009/0112125 A1 | 4/2009 | Tamir |
| 2010/0174211 A1 | 7/2010 | Frey et al. |
| 2012/0123297 A1 | 5/2012 | Brancazio |
| 2013/0172698 A1 | 7/2013 | Reynolds et al. |
| 2013/0190792 A1 | 7/2013 | Hostettler et al. |
| 2014/0341787 A1 | 11/2014 | Johnson et al. |
| 2015/0094914 A1 | 4/2015 | Johnson et al. |
| 2016/0375223 A1 | 12/2016 | Averni et al. |
| 2017/0035336 A1* | 2/2017 | Wilkinson ....... A61B 5/150786 |
| 2017/0122846 A1 | 5/2017 | Holmes et al. |
| 2017/0172481 A1 | 6/2017 | Berthier et al. |
| 2017/0246625 A1 | 8/2017 | Becker et al. |
| 2017/0347934 A1 | 12/2017 | Kuester |
| 2019/0000365 A1* | 1/2019 | Beyerlein ........ A61B 5/150442 |
| 2021/0137435 A1* | 5/2021 | Queval ............ A61B 5/150236 |
| 2023/0146889 A1* | 5/2023 | Queval ............. A61B 5/15113 600/577 |

FOREIGN PATENT DOCUMENTS

| | | | |
|---|---|---|---|
| CN | 201505140 U | 6/2010 | |
| CN | 104107054 A | 10/2014 | |
| CN | 104968269 A | 10/2015 | |
| CN | 105208994 A | 12/2015 | |
| CN | 106456439 A | 2/2017 | |
| CN | 107496033 A | 12/2017 | |
| JP | 2009542304 A | 12/2009 | |
| JP | 2014501555 A | 1/2014 | |
| JP | 2017006184 A | 1/2017 | |
| WO | WO-2014145935 A1 * | 9/2014 | ......... A61B 10/0045 |
| WO | 2018022535 A1 | 2/2018 | |

OTHER PUBLICATIONS

Japanese Patent Office, Office Action Issued in Application No. 2020-564702, Jan. 24, 2023, 21 pages. (Submitted with Machine Translation).

China National Intellectual Property Administration, Office Action and Search Report Issued in Application No. 201980032202.5, Jan. 25, 2024, 14 pages. (Submitted with Partial Translation).

* cited by examiner

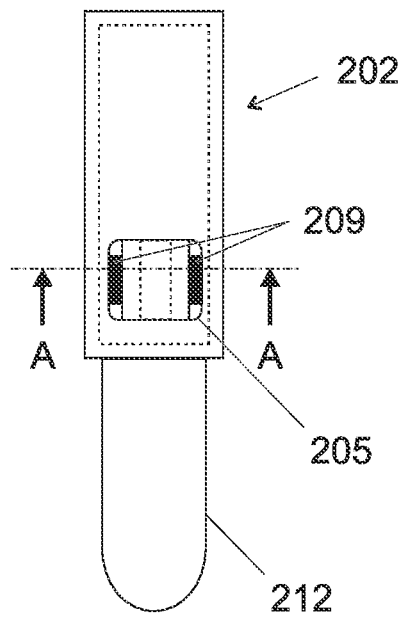 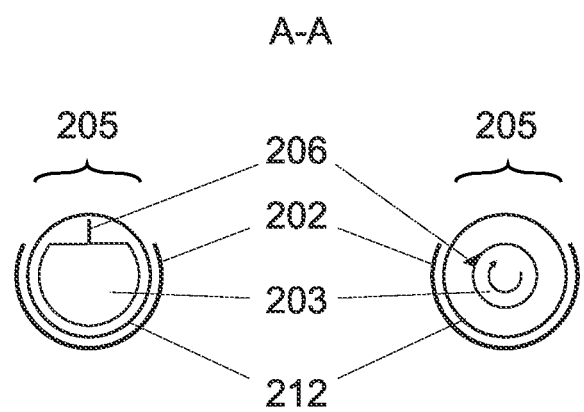
Fig. 27A  Fig. 27B  Fig. 27C

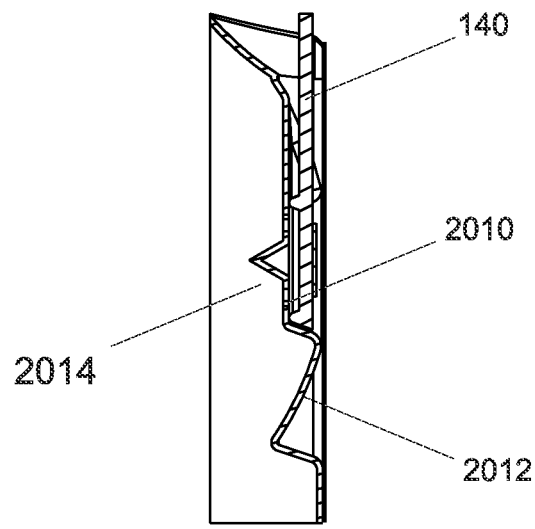
Fig. 38
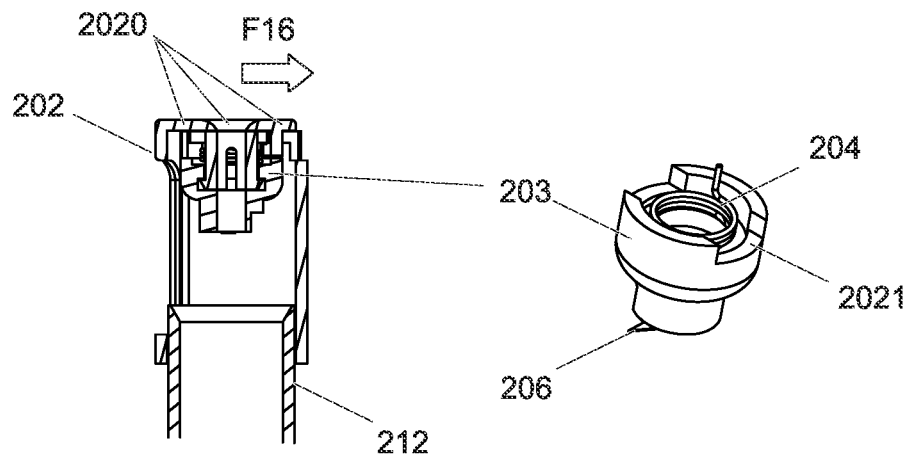
Fig. 39
Fig. 40

SAMPLE COLLECTION DEVICE, SYSTEM AND METHOD FOR EXTRACTING AND COLLECTING A SAMPLE OF A FLUID OF A USER

CROSS-REFERENCE TO RELATED APPLICATIONS

The present application is a U.S. National Phase of International Application No. PCT/IB2019/053986, entitled "SAMPLE COLLECTION DEVICE, SYSTEM AND METHOD FOR EXTRACTING AND COLLECTING A SAMPLE OF A FLUID OF A USER," and filed on May 14, 2019. International Application No. PCT/IB2019/053986 claims priority to Swiss Patent Application No. 00595/18 filed on May 14, 2018. The entire contents of each of the above-listed applications are hereby incorporated by reference for all purposes.

TECHNICAL FIELD

The present invention concerns a sample collection device for collecting a sample of a fluid of a user, e.g. blood, in particular capillary blood. The present invention concerns also a system and a method for extracting and collecting this sample.

BACKGROUND AND SUMMARY

Venepuncture is a blood collection method where the vein is punctured by a hollow needle, and where blood is collected into a tube. This method allows collection of large and high quality blood samples into tubes. Several tubes can be filled during one blood sampling. Furthermore, these tubes are compatible with highly automated blood analysers, which can analyse thousands of samples per day. These high throughput capabilities answer the growing need to fast and clinical grade diagnostics at the lowest cost.

However, this method requires a healthcare professional (e.g. a nurse) with a specific qualification and a dedicated infrastructure. Moreover, risks are associated with puncturing the vein: if the vein is fragile or if the procedure is not performed properly, it can result in a hematoma. There is also a risk of needle-stick injury, which may expose the healthcare professionals to blood-borne diseases.

On the other hand, the finger prick method consists in the incision of the skin at the fingertip using a lancet. A drop or a few drops of capillary blood can be collected into capillary tubes or into dedicated analytical devices (e.g. microfluidic devices, lab-on-chip, paper-based diagnostic tools, . . . ). While this technique does not require highly trained professional and can be performed by the patient himself, it is very difficult to collect blood above 100 µl and to perform many analyses per sample. Moreover, the blood collected into glass capillaries or through other devices, can not be analysed by automated analysers, used by central laboratories, which require to have a minimum blood volume of 100 µl to 200 µl contained into a single tube.

In some instances, more blood, up to 0.5 ml, can be collected with the finger prick method. However, this requires to press and squeeze the finger in order to collect more blood. Squeezing too hard may result in haemolysis (damage of the red blood cells) and dilution of the blood sample by the interstitial fluid, contained in spaces between the tissue cells. For these reasons, and to keep a good blood quality, the use of finger prick is generally limited to the collection of small volumes of blood.

The document U.S. Pat. No. 6,283,926 describes a method and a device for obtaining samples of blood for diagnostic purposes. The device comprises a vacuum pump, which requires a source of power, and a micro-controller arranged to drive the pump and the lancet based on the signal from a pressure sensor. The lancet of this device moves in a direction perpendicular to the skin of the user. This device is complicated, as it comprises several electronics components. Moreover, it is arranged to draw relatively small blood volumes (1 µl).

An aim of the present invention is to propose a sample collection device which simplifies the collection of a fluid of a user, e.g. blood, while keeping a high-quality standard for its analysis.

Another aim of the present invention is to propose a sample collection device which is safer for the user or for an operator (e.g. a nurse) that minimizes the risk of injury by handling it.

Another aim of the present invention is to propose a sample collection device which reduces the risk of contamination of the collected sample.

Another aim of the present invention is to propose a sample collection device which is compatible with standard blood analysers of central laboratories.

Another aim of the present invention is to propose a system for extracting and collecting a user fluid sample which can be used without the need of high-skill training, for example which can be used by the user him-self (i.e. a patient).

Another aim of the present invention is to propose a system for extracting and collecting a user fluid sample which requires minimal action from the user.

Another aim of the present invention is to propose a system for extracting and collecting a user fluid sample which can collect about 0.5 ml to 2 ml of fluid, e.g. 1 ml of fluid.

Another aim of the present invention is to propose a system for extracting and collecting a user fluid sample which is as painless as possible.

Another aim of the present invention is to propose a system for extracting and collecting a user fluid sample which avoids and/or prevents cross contamination of the fluid sample.

According to the present disclosure, these aims are achieved by means of the sample collection device, the system and the method for extracting and collecting a sample of a fluid of a user according to the embodiments described herein.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE FIGURES

The invention will be better understood with the aid of the description of an embodiment given by way of example and illustrated by the figures, in which:

FIG. 27A shows a front view of a part of the sample collection device according to one embodiment of the invention.

FIG. 27B shows one embodiment of a section view of the part of the sample collection device of FIG. 27A.

FIG. 27C shows another embodiment of a section view of the part of the sample collection device of FIG. 27A.

FIG. 38 shows a part of a cross-section view of the embodiment of the system of FIG. 36.

FIG. 39 shows another part of another cross-section view of the embodiment of the system of FIG. 36.

FIG. 40 shows a perspective view of one embodiment the triggering and incision mechanisms of system of FIG. 36.

Similar reference numerals may have been used in different figures to denote similar components. FIGS. 1-9, 10A, 10B, 30-40, 41A, and 41B are shown with components in proportional size with one another, according to some embodiments.

DETAILED DESCRIPTION

In the following description provided by way of example, reference will be made, for reasons of simplicity, to system for collecting and extracting the blood of a user, comprising a blood collection device and a blood extraction device. However, it must be understood that the invention is not limited to such a fluid, but includes collection devices and extraction devices, both being arranged to collect other kinds of fluid, in particular bodily fluids.

In the following description provided by way of example, reference will be made, for reasons of simplicity, to "sample collection device" and "sample extraction device". However, it must be understood that the "sample" indicated in those expressions is a sample of a fluid, in particular a bodily fluid, e.g. blood, in particular capillary blood.

The system 300 for extracting and collecting a sample of a fluid of a user according to the invention comprises two parts:
 a sample collection device 200; and
 a sample extraction device 100.

In one advantageous embodiment, the sample collection device 200 is consumable and the sample extraction device 100 is on the contrary reusable. In another embodiment, the sample extraction device 100 is also a consumable. In this case, the sample collection device 200 and the sample extraction device 100 can form one single system 300 that is consumable. An example of such consumable system 300 will be discussed with reference to FIG. 36.

We will describe first the features of sample collection device 200, secondly the features of sample extraction device 100 and at the end the method and system of collecting and extracting such a sample.

Figure 1:
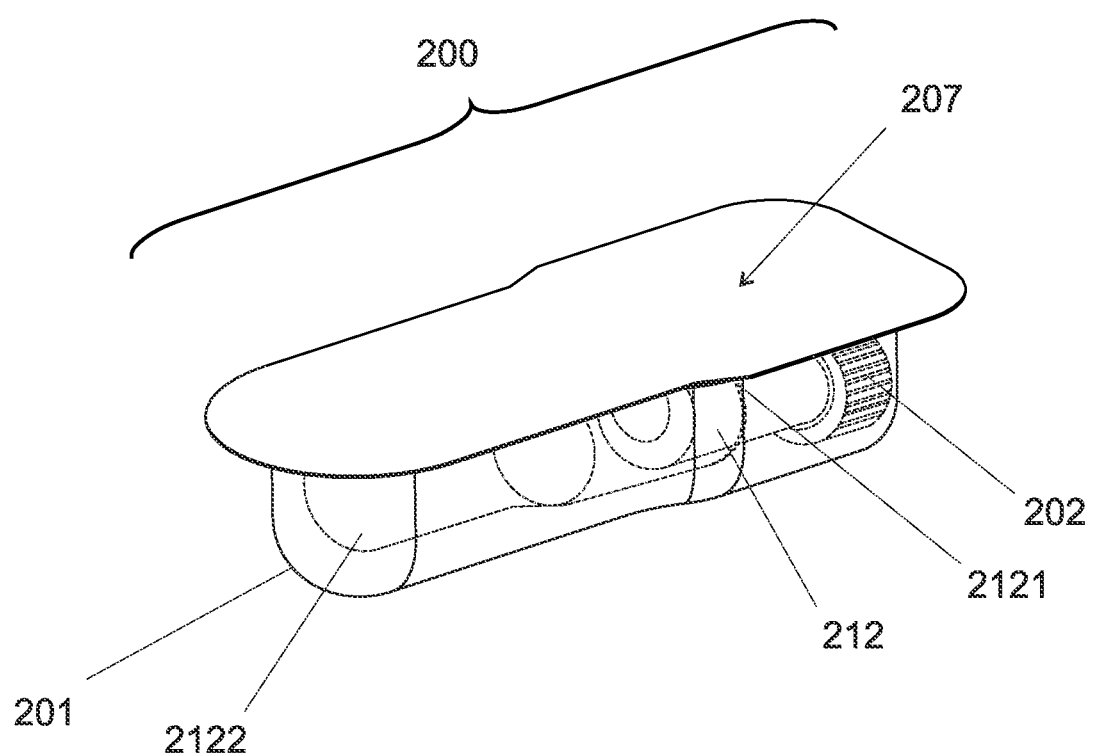
FIG. 1 shows a perspective view of a part of the sample collection device according to one embodiment of the invention.

FIG. 1 shows a perspective view of a part of the sample collection device 200 according to one embodiment of the invention.

The sample collection device 200 according to the invention comprises:
 a sample container 212 arranged to receive the sample and comprising an open end 2121;
 a cap 202 arranged to cooperate with the sample container 212 so as to close the open end 2121.

In the embodiment of FIG. 1, the sample container 212 is a tube, having substantially a cylindrical shape and comprising the open end 2121 and a closed end 2122 with a substantially spherical shape.

In a particular embodiment, the tube is a "standard" tube, i.e. a tube compatible with standard blood analysers of central laboratories. For example, the diameter of the standard tube belongs to the range 12 mm-16 mm, e.g. it is equal to 13 mm.

In one embodiment, the length of the tube is compatible with standard blood analysers of central laboratories. In another embodiment, the length of the tube is less than a standard length, i.e. a length compatible with standard blood analysers of central laboratories. In such a case, the tube can comprise connection means so as to connect it with an extension tube, so that the total length of the set comprising the tube and the extension tube is a standard length, for example a length ranging from 50 mm to 120 mm, e.g. equal to 75 mm. In another embodiment, this extension tube could also correct the final diameter of the tube. The diameter of the tube could be smaller than the standard diameter, but it could be adjusted with a larger extension tube, so as to be compatible with standard blood analysers of central laboratories. In one embodiment, those-connection means for connecting the tube with the extension tube are arranged such that they allow an easy connection of the tube with the extension tube, but they prevent or render difficult the disconnection of the extension tube from the tube. This feature is useful in particular if a label identifying the fluid sample is placed on the outer surface of the extension tube, so as to prevent a user from detaching the extension tube from the tube; the traceability of the fluid sample is then guaranteed. In one embodiment, those connection means comprise clip means and/or screwing means.

In a particular embodiment, the tube is arranged for receiving at least 0.5 ml, and preferably 1 ml, of fluid sample, as will be discussed.

In the embodiment of FIG. 1, the sample container 212 is (at least partially) transparent, so as to directly see its content.

In the embodiment of FIG. 1, the cap 202 is also a "standard" cap i.e. a cap compatible with standard blood analysers of central laboratories. For example, the diameter of the outer part of the standard cap is 15 mm.

In the embodiment of FIG. 1, the sample container 212 and its cap 202 are placed in a suction pack 201. The size and the shape of the suction pack 201 are therefore arranged to receive the sample container 212 and the cap 202. In one embodiment, the suction pack 201 is made, at least in part, of a flexible material.

The suction pack 201 has two main functions:
 1) it is used as a packaging for the sample container 212 and its cap 202;
 2) it serves as a suction cup in which vacuum is applied for user's skin suction and fluid collection, as will be discussed.

In the embodiment of FIG. 1, the suction pack 201 comprises a lid 207, so as to guarantee the sterilisation of its content and/or a barrier from moisture. This lid 207 is removable. In one embodiment, it is a semi-permeable membrane that permits to maintain the inside of the suction pack 201 sterilized, for example Tyvek®. In another embodiment, the lid 207 is non-permeable: this allows to keep an airtight environment during storage and/or transport so as to prevent humidity from entering the suction pack 201 and/or the sample container 212. In fact, humidity could affect the stability of the additives present in the sample container 212.

In the embodiment of FIG. 1, the suction pack 201 is also (at least partially) transparent, so as to give a good visual indication of the integrity of its content. Before the use, the user (or an operator, e.g. a nurse) can indeed check that the lid 207 of the suction pack 201 has not been open yet, as an indication that its content is still sterilized and safe to be used.

In one example, the suction pack 201 is made for instance of polycarbonate, PET-G, etc. so that a user or an operator can track progress of fluid collection by optically monitoring the level of the fluid sample in the sample container 212.

As will be discussed, in one embodiment the suction pack 201 comprises a semi-permeable membrane allowing the vacuum to enter in the suction pack.

In one embodiment, the suction pack 201 comprises or it is made (at least partially) of materials enhancing the sealing between suction pack 201 and the skin of the user, so as to guarantee a good sealing between the skin and the suction pack 201.

In one embodiment, the suction pack 201 is a blister pack. Consumables in blister packs is common practice in healthcare. The advantage of a blister packaging is that it is cost-effective, it can be closed by a removable lid 207, and can be transported and handled while preserving sterilization of its content.

Figure 8:
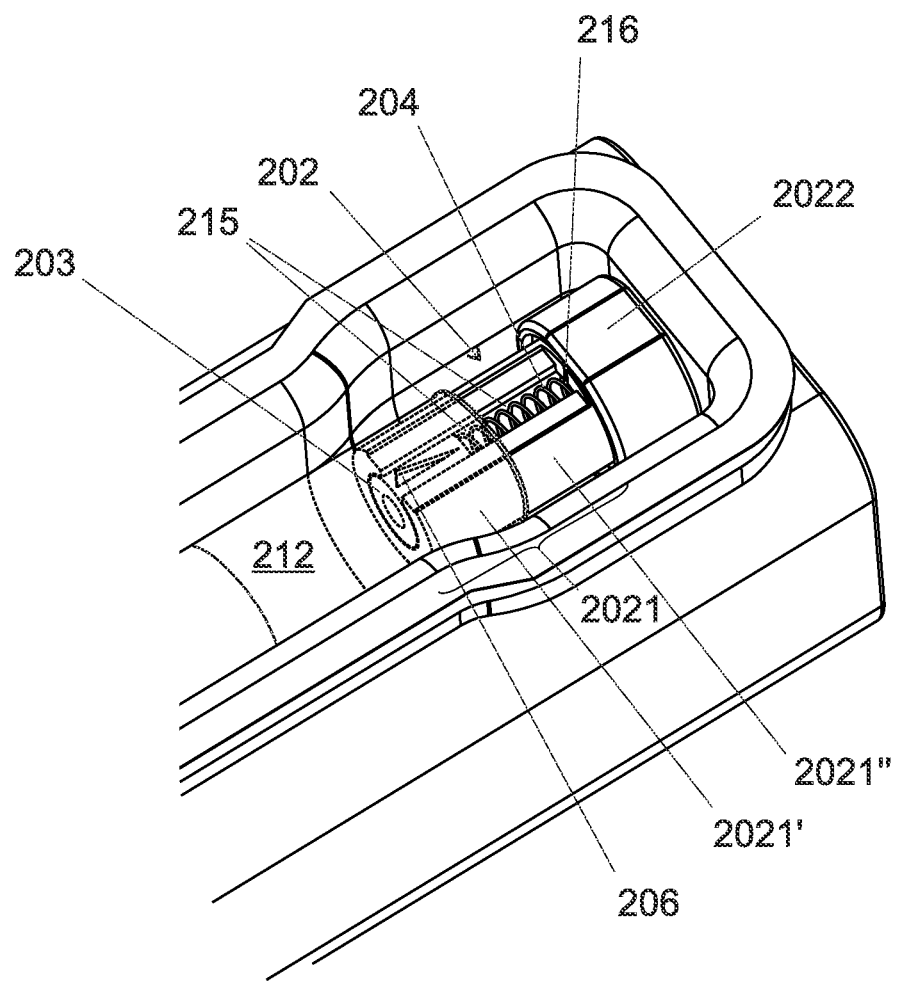
FIG. 8 shows a perspective view of a part of an embodiment of the system according to the invention, wherein the incision mechanism is in the first incision mechanism position.
Figure 9:
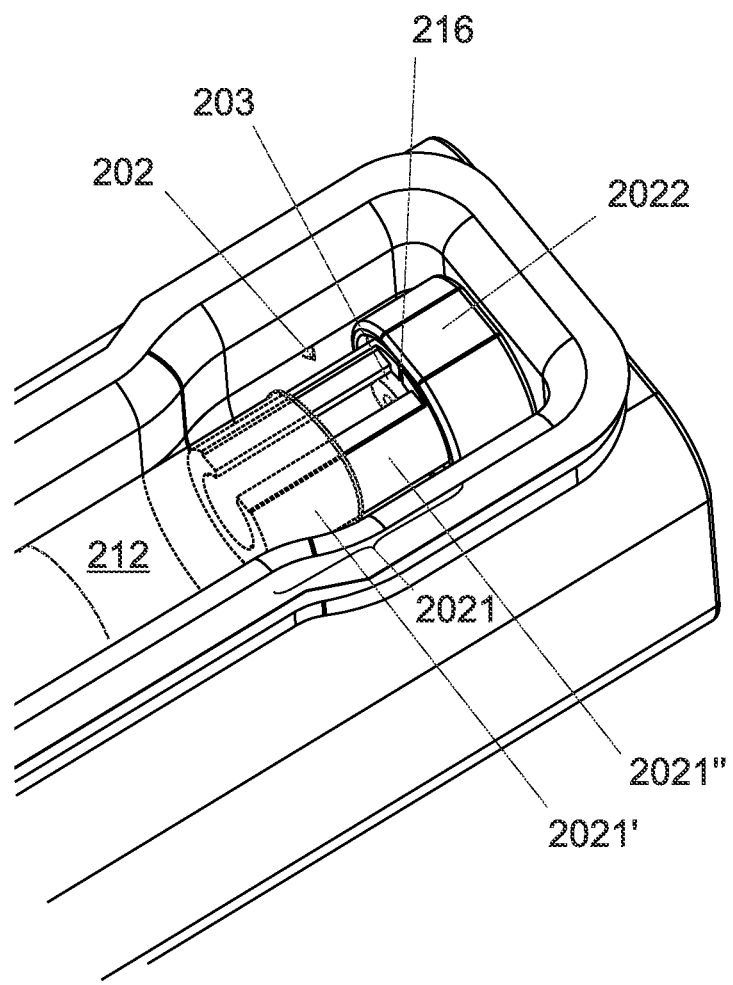
FIG. 9 shows a perspective view of a part of the embodiment of the system of FIG. 8, wherein the incision mechanism is in the second incision mechanism position.
Figures 10A, 10B:
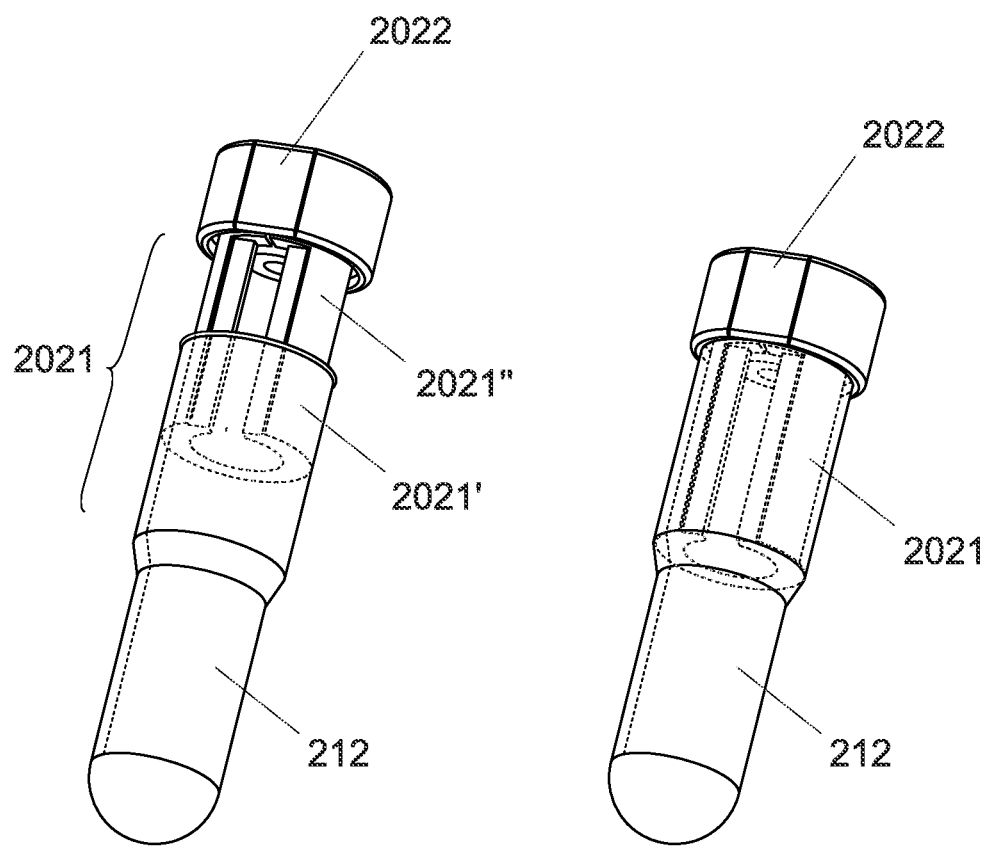
FIG. 10A shows a perspective view of one embodiment of a part of the sample collection device according to one embodiment of the invention, wherein the cap is in the first cap position.
FIG. 10B shows a perspective view of one embodiment of the part of the sample collection device of FIG. 10A, wherein the cap is in the second cap position.
Figures 11A, 11B, 11C:
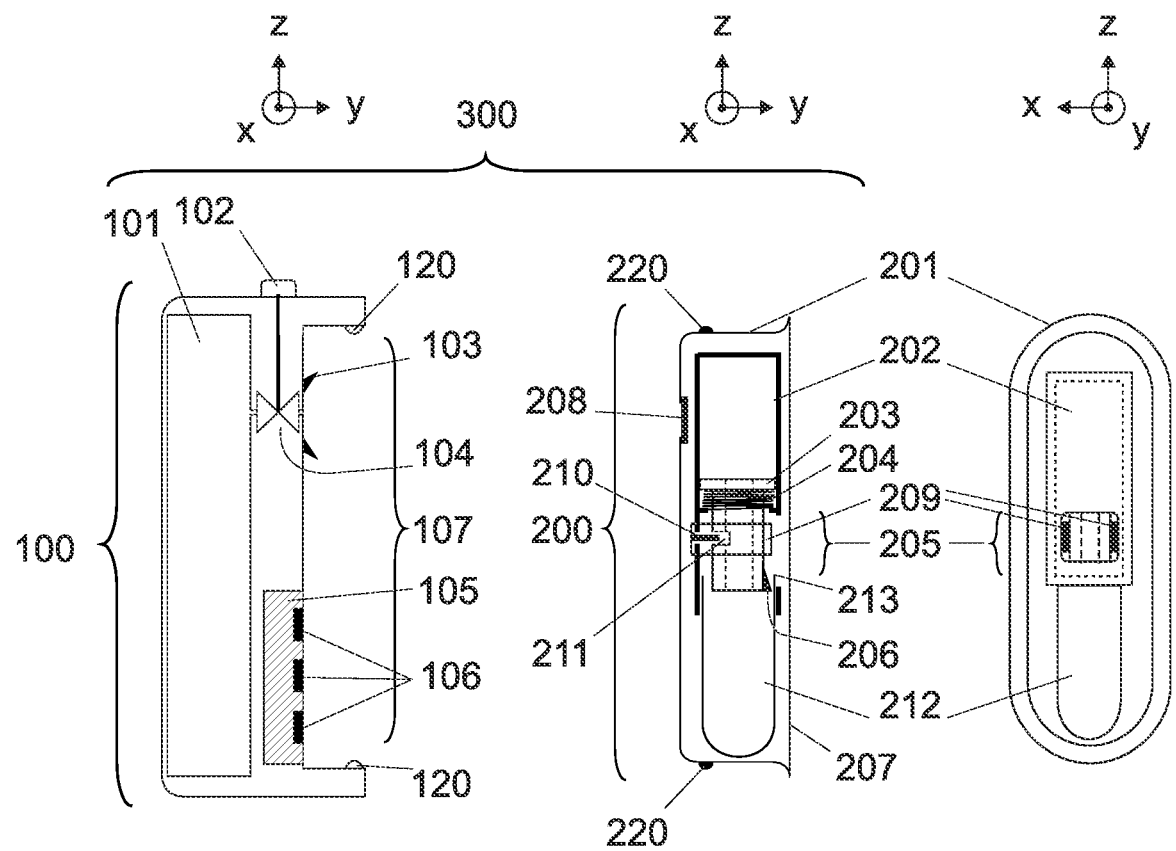
FIG. 11A shows a cross-section view of one embodiment of the sample extraction device of the system for extracting and collecting a sample of a fluid of a user according to the invention.
FIG. 11B shows a cross-section view of one embodiment of the sample collection device according to the invention.
FIG. 11C shows a front view of the embodiment of the sample collection device of FIG. 11B.

According to the invention, the cap 212 comprises:
- a collection window 205, visible e.g. in FIGS. 8, 11B and 11C and arranged to enter in contact with an area or part of the user to be incised;
- a triggering mechanism; and
- an incision mechanism movable in the cap 202 by this triggering mechanism from a first incision mechanism position (illustrated for example in FIG. 8) to a second incision mechanism position (illustrated for example in FIG. 9).

Advantageously, during this moving the incision mechanism is arranged to incise at the collection window 205 the user so as to exit the sample from the user. During the moving from the first incision mechanism position to the second incision mechanism, the cap 202 is always in a first cap position, illustrated for example in FIGS. 1, 8, 9 and 10A.

In fact, according to the invention, the cap 202 itself is arranged to be moved on the sample container 212 from a first cap position (illustrated for example in FIG. 1, 8, 9 or 10A) to a second cap position (illustrated for example in FIG. 10B), wherein in both the first and in the second cap positions the open end 2121 of the sample container 212 is at least partially in contact with the sample container 212 so as to guide the movement of the cap 202 from the first cap position to the second cap position. In the illustrated embodiment, which is not limitative, in both the first and in the second cap positions the open end 2121 of the sample container 212 is closed by the cap 202.

According to the invention, the cap 202 comprises also a sealing mechanism (not illustrated), so as so seal the sample container when the cap is in the second cap position (illustrated for example in FIG. 10B), so as to safely transport the sample.

Since the fluid is collected with a sufficient amount (about 1 ml), conditioned into a sample container 212 with a cap 202, both matching standards (container size, cap format, and/or additives required for the different types of analyses) used for standard blood analysers, and safely transported, several analyses can be performed from one sample of fluid collected with the device according to the invention.

The collection device according to the invention has therefore the following advantages:
- the cap 202 integrates the incision mechanism;
- the same cap allows to seal the sample container 212 after the fluid sample has been collected, so as to safely transport this fluid sample; and
- the fluid, e.g. blood, is directly collected into the sample container 212 used for its transport and analysis, as the fluid falls down directly into the sample container 212.

It must be noted that the movement of the incision mechanism requires no active actions from the user: in fact, it is triggered by a triggering mechanism in an automatic way, as will be described.

In a particular embodiment, the movement of the cap 202 is manually performed by the user or by an operator. However, in another embodiment, it is automatically performed as well.

In one preferred embodiment, visible for example in FIGS. 8 and 9, the cap 202 comprises a first cap portion 2021 and a second cap portion 2022. The two portions 2021, 2022 can be two distinct parts connected together by connecting means (not illustrated). In another embodiment, the cap 202 is monobloc, i.e. it is made by a single piece comprising those two portions 2021, 2022.

In one embodiment, the first cap portion 2021 comprises the collection window 205.

As visible in FIGS. 8 and 9, the first cap portion 2021 comprises an opening 215, along the main direction of the first cap portion 2021. In other words, since this opening 215 is present, the first cap portion 2021 has a cross section with a substantially C shape.

In the illustrated embodiment, at least a part 2021' of this first cap portion 2021 is inserted during all the time of the working of the system 300 in the sample container 212, so as to close the open end 2121 of the sample container 212 during the moving of the incision mechanism.

Another part 2021" of this first cap portion 2021 is outside of the sample container 212, when the cap 202 is in its first position, as illustrated in FIG. 8.

In one embodiment, the second cap portion 2022 has a size larger than the size of the first cap portion 2021. It is not adapted to enter into the sample container 212, but rather to seal it.

In one embodiment, the second cap portion 2022 comprises the above-mentioned sealing mechanism.

In one embodiment, the second cap portion 2022 comprises a cavity 216, visible in FIGS. 8 and 9, for receiving the incision mechanism, and in particular the cutting element 206, once the incision mechanism is in the second incision mechanism position (illustrated in FIG. 9), so that the incision mechanism is irreversibly and safely retracted in this cavity 216 so that it can no longer incise the user.

In one embodiment, at least a part of the cap 202 is accessible by the user or by an operator, so as to manually extract the fluid sample from the sample container 212, without detach the cap 202 from the sample container 212.

In one embodiment, the incision mechanism comprises:
- a support element 203; and
- an elastic element 204.

In one preferred embodiment, the support element 203 is a piston, which is for example visible in FIGS. 8 and 11B; this support element is connected, preferably directly connected, to a cutting element 206, so as once the support element 203 is moved, the cutting element 206 is moved as well.

The cutting element 206 can be a blade, a lancet, or any other element capable of forming an opening in the skin of a user.

In one preferred embodiment, the elastic element 204 is a spring, which is for example visible in FIGS. 8 and 11B; this elastic element 204 is blocked before the use of the system according to the invention, for example in a compressed position. Once the incision mechanism is triggered, the elastic element 204 is free to be decompressed, and this decompression moves the support element 203 and then the cutting element 206 from the first incision mechanism position (visible e.g. in FIG. 8) to the second incision mechanism position (visible e.g. in FIG. 9).

It must be understood that the present invention is not limited to a compression elastic element only, i.e. an elastic element (e.g. a spring) that can be compressed and decompressed, but it concerns also other elastic elements, e.g. torsion and/or traction elastic elements, i.e. elastic elements (e.g. springs) that can perform a movement of torsion and/or traction.

As visible in FIG. 8, when the incision mechanism is in the first incision mechanism position, the cutting element 206 is in the sample container 212, so as to ensure the safety of the user and/or of an operator.

In the embodiment of FIGS. 8 and 9, the movement of the incision mechanism from the first incision mechanism position to the second incision mechanism position is a linear movement (i.e. a translation) performed in a direction parallel to a surface of the user to be incised, as illustrated in FIG. 27B.

However, in another alternative embodiment, the movement of the incision mechanism from the first incision mechanism position to the second incision mechanism position is a circular movement (i.e. a rotation), as illustrated in FIG. 27C, wherein the axis of rotation of this circular movement is preferably a main axis of the sample container 212. For example, this circular movement is possible if the elastic element 204 is a torsion elastic element 204. Another example of such circular movement will be discussed with reference to the embodiment of FIG. 36.

The triggering mechanism of the sample collection device comprises a triggering element, which is visible in for example in FIGS. 11B and 11C. This triggering mechanism comprises a triggering element 209, which in the illustrated embodiment is a half-ring surrounding at least a part of the support element 203.

In particular, the triggering element 209 comprises a protrusion 210, e.g. a finger, which is arranged to be received by a corresponding cavity 211 in the support element 203, so as to hold the triggering element 209 in the first triggering element position visible in, for example, FIG. 11B.

In the illustrated embodiment, the cap 202 comprises the triggering mechanism, in particular the triggering element 209. In another alternative embodiment, not illustrated, the support element 203 comprises the triggering mechanism, in particular the triggering element 209.

As will be discussed, once the system 300 according to the invention is on the user's skin, it is arranged to deform and/or stretch a part of the user's skin so that this deformed and/or stretched part will move the triggering element 209 from a first triggering element position (visible e.g. in FIG. 17), wherein it holds the elastic element 204 in a compressed position and the support element 203 in a fixed position in the sample container 212, to a second triggering element position (visible e.g. in FIG. 18), wherein the triggering element 209 no longer holds the elastic element 204 nor the support element 203.

Figure 5:
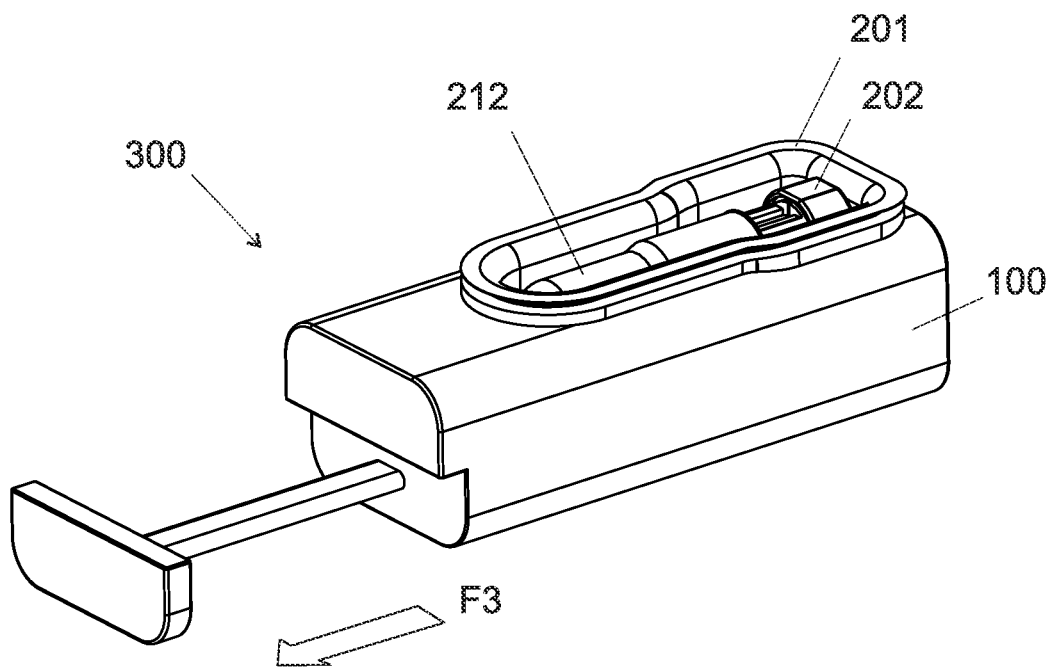
FIG. 5 shows a perspective view of the system of FIG. 4, wherein its vacuum creation mechanism is in a first position.
Figure 6:
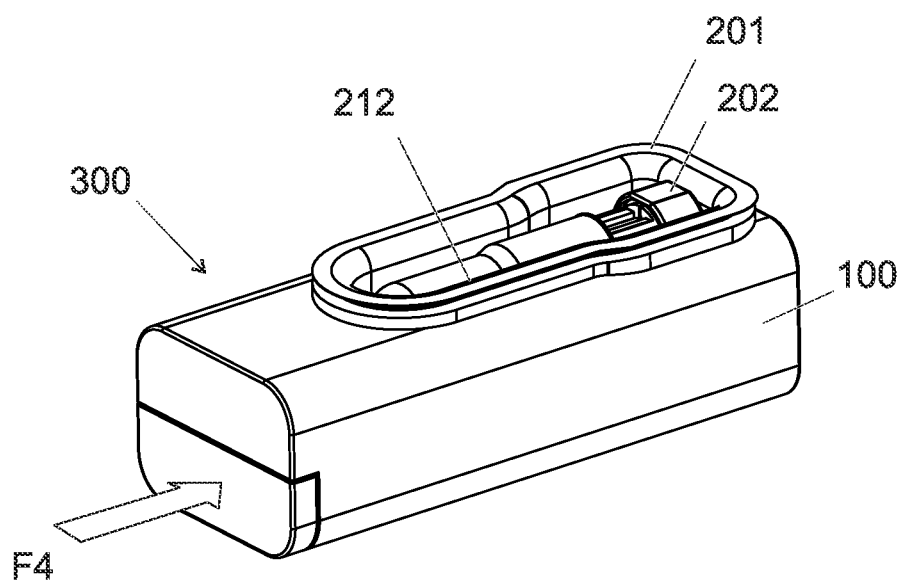
FIG. 6 shows a perspective view of the system of FIG. 4, wherein its vacuum creation mechanism is in a second position.

We describe now the sample extraction device. As visible for example in FIG. 11A, it comprises
- a port 107 (e.g. a cavity or a recess) arranged to receive at least a part of the collection device 200;
- a vacuum chamber 101;
- a vacuum creation mechanism 108 arranged to create vacuum in the vacuum chamber 101; a non-limitative example of such vacuum creation mechanism is illustrated in FIGS. 5 and 6; the vacuum creation mechanism is preferably completely mechanical and devoid of electronics component;
- a valve (or an assembly of valves) 104 arranged to close and/or open the vacuum chamber 101 and/or to release the sample collection device (200) to atmospheric pressure; and
- a valve control mechanism 102 arranged to command the valve 104 (or the assembly of valves) so as to transfer the vacuum from the vacuum chamber 101 to the collection device 200, but also to release the collection device 200 to atmospheric pressure, in particular after collection.

In the present context the term "vacuum" indicates an area with a gaseous pressure much less than the atmospheric pressure, e.g. with a gaseous pressure between −70 kPa and −20 kPa compared to the atmospheric pressure, e.g. of about −40 kPa.

In one preferred embodiment, the valve control mechanism 102 is a button, e.g. a push button, or an assembly of buttons. In one preferred embodiment, it is arranged to control three modes of the valve 104, i.e. open, closed, release.

In one preferred embodiment, the sample extraction device comprising an electronic module 105, visible e.g. on FIG. 11A, comprising a communication module (not illustrated) and a power supply (not illustrated).

In another preferred embodiment, visible e.g. on FIG. 11A, the sample extraction device comprises at least a sensor 106, e.g. an optic sensor, for detecting a predetermined sample volume in the sample container.

In another preferred embodiment, the sample extraction device comprises an alerting mechanism (not illustrated), indicating to the user the end of the sample extraction, e.g. by an audio and/or visible signal.

In another preferred embodiment, the sample extraction device comprises a gasket 103, visible e.g. on FIG. 11A, cooperating with the area of the sample collection device 200 comprising a membrane 208. In one variant, the membrane 208 is semi-permeable. In another variant, the membrane 208 is non-permeable: this allows to keep an airtight environment during storage and/or transport so as to prevent humidity from entering the suction pack 201 and/or the sample container 212. In fact, humidity could affect the stability of the additives present in the sample container 212.

We describe now the method for collecting and extracting a sample of a fluid of the user, with the system according to the invention.

In one embodiment, the cap 202 is placed in and/or on the sample container 212, so as to close its open end 2121, as illustrated in FIG. 1. Then, the sample container 212 and the cap 202 are packaged in the suction pack 202, the suction pack 202 is closed by a lid 207 and the closed suction pack 202, comprising the sample container 212 and the cap 202, is sterilized.

In an embodiment, the sample collection device 200 is consumable and the sample extraction device 100 is not consumable. A new sample collection device 200 is then placed on or in the sample extraction device 100, in particular in a port 107 of the sample extraction device 100, visible in FIG. 11A.

The sample collection device 200 is then mechanically connected to the sample extraction device 100, e.g. by using first and second connection means 120 respectively 220, illustrated in FIGS. 11A and 11B. Those means guarantee a connection by clips, but of course any other kind of means guaranteeing a mechanical connection between the sample collection device 200 and the sample extraction device 100 can be used, e.g. and in a non-limiting way a magnet on a device and a ferromagnetic area on the other device, a screw or a rivet in a device and a hole in the other device, docking means, etc.

Figure 12:
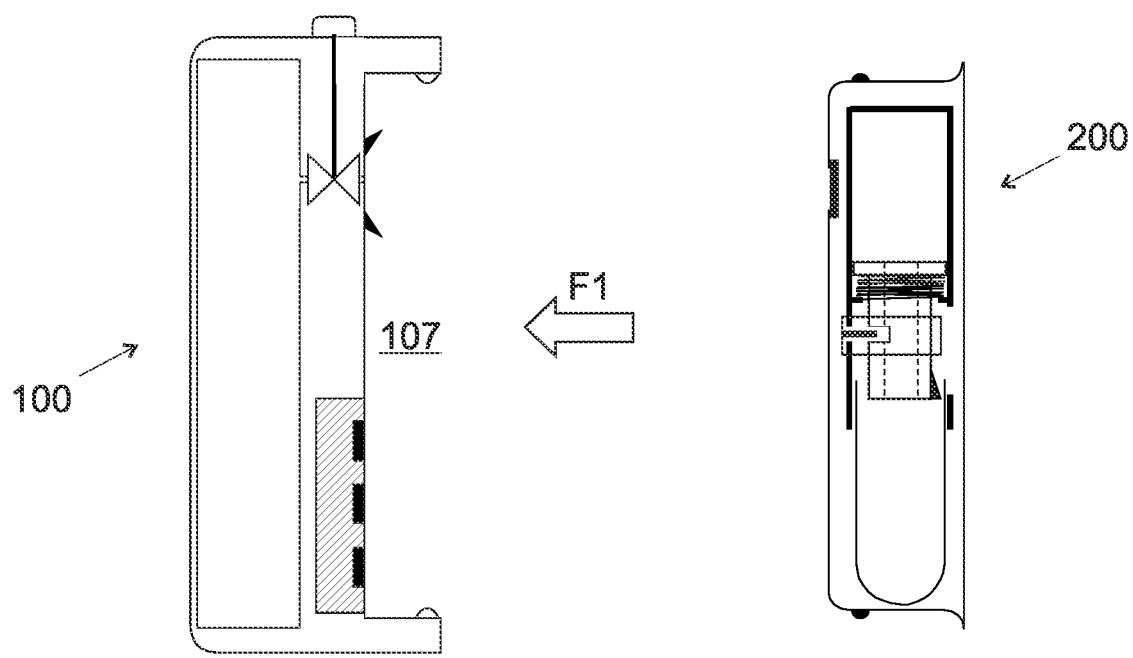
FIG. 12 shows a cross-section view of one embodiment of the system for extracting and collecting a sample of a fluid of a user according to the invention, wherein the sample collection device is inserted inside the sample extraction device.
Figure 13:
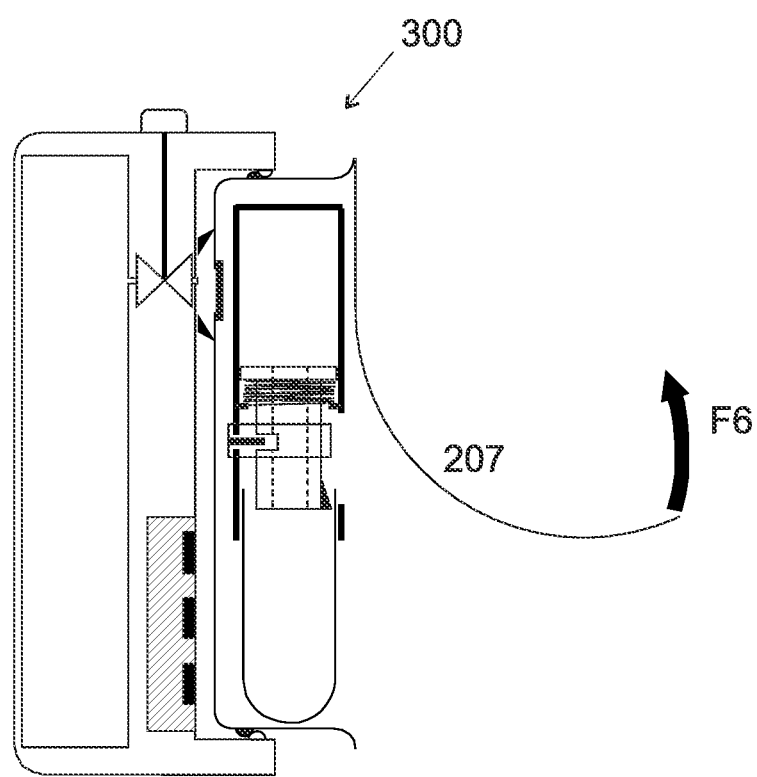
FIG. 13 shows a cross-section view of the embodiment of the system of FIG. 12, wherein the lid of the sample collection device is removed.

FIG. 12 shows a cross section view of one embodiment of the system for 300 extracting and collecting a sample of a fluid of a user according to the invention, before that the sample collection device 200 is inserted in the port 107 of the sample extraction device 100. The arrow F1 indicates the movement of the sample collection device 200 to the sample extraction device 100.

The sample collection device 200 and the sample extraction device 100 form the system 300 according to the invention.

Although FIG. 12 illustrates an embodiment in which the sample collection device 200 is moved to the extraction device 100 in the direction of the arrow F1, this embodiment is not limitative and other possibilities can be imagined by the skilled person. For example and in a non-limitative way, the sample collection device 200 could be slid in some (not illustrated) rails of the extraction device 100 in a direction perpendicular to the direction of the arrow F1. In such a case, the illustrated first and second connection means 120 respectively 220 will be modified accordingly.

Figure 2:
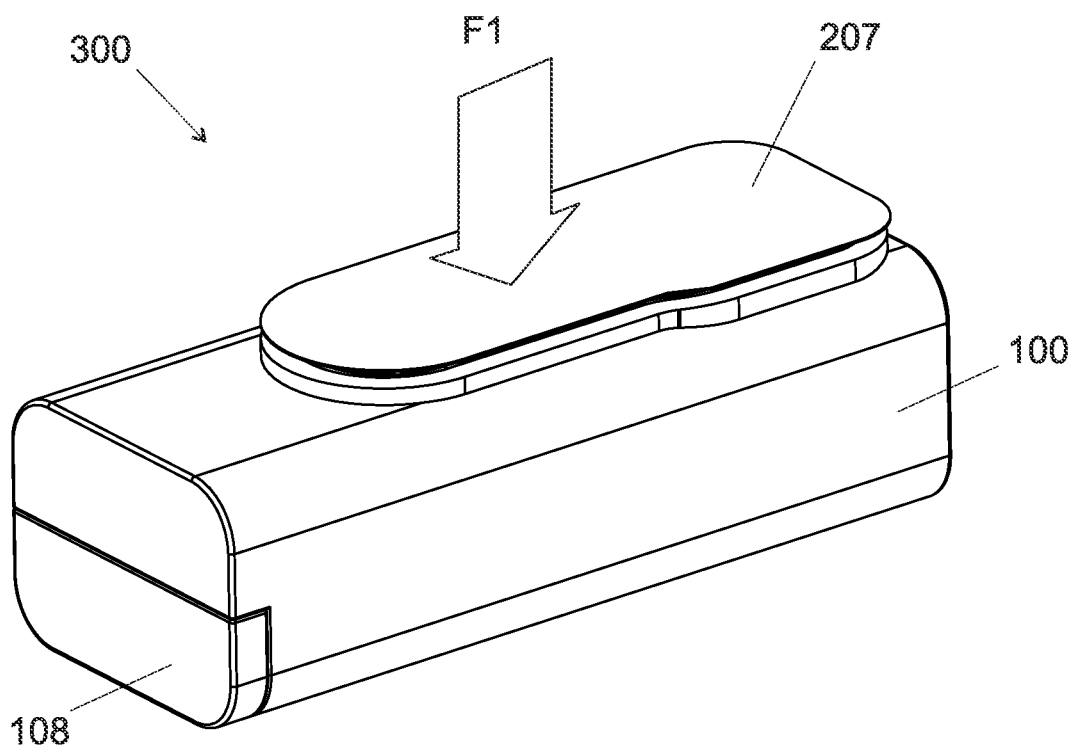
FIG. 2 shows a perspective view of the system for extracting and collecting a sample of a fluid of a user according to one embodiment of the invention.

FIG. 2 shows a perspective view of this system 300 according to one embodiment of the invention. In this case, the arrow F1 indicates the movement of the sample collection device 200 to the sample extraction device 100.

It must be noted that the sample collection device 200 and the sample extraction device 100 are arranged so that, when connected, the valve 104 and the possible gasket 103 of the sample extraction device 100 are placed in correspondence of the membrane 208 of the sample collection device 200; moreover, where present, the sensor(s) 106 of the sample extraction device 100 is(are) placed in correspondence of the sample container 212 of the sample extraction device 100.

The system 300 according to the invention is portable. Its size allows it to be easily handled by a hand of a user. In the embodiment of FIG. 2, it is substantially a parallelepiped. However, other shapes are possible, e.g. a cylindrical shape. In another embodiment, its length is in the range of 5 cm to 20 cm, e.g. 10 cm.

Figure 3:
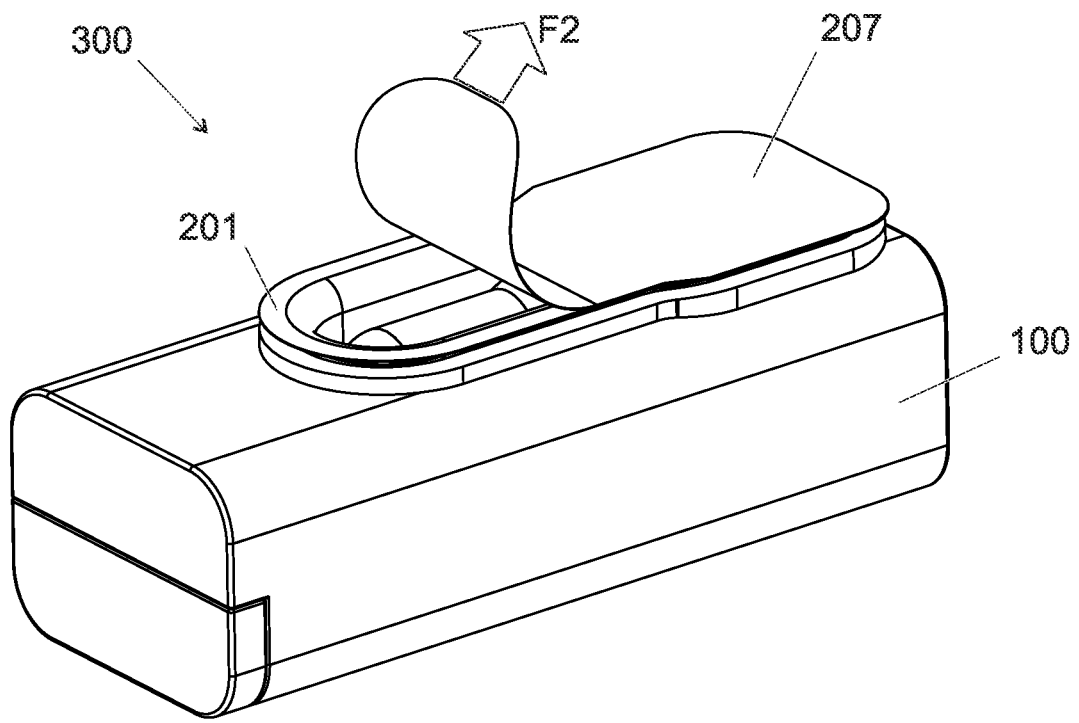
FIG. 3 shows a perspective view of the system of FIG. 2, and in particular the removing of its lid.

Then, the user (or an operator) removes the lid 207 of the suction pack 201, as illustrated in FIG. 3 (arrow F2) or 13 (arrow F6). The lid 207 guarantees the sterilisation of its content. As will be discussed, a membrane 208 of the collection device 200 contributes as well to prevent cross contamination of the fluid sample.

Figure 4:
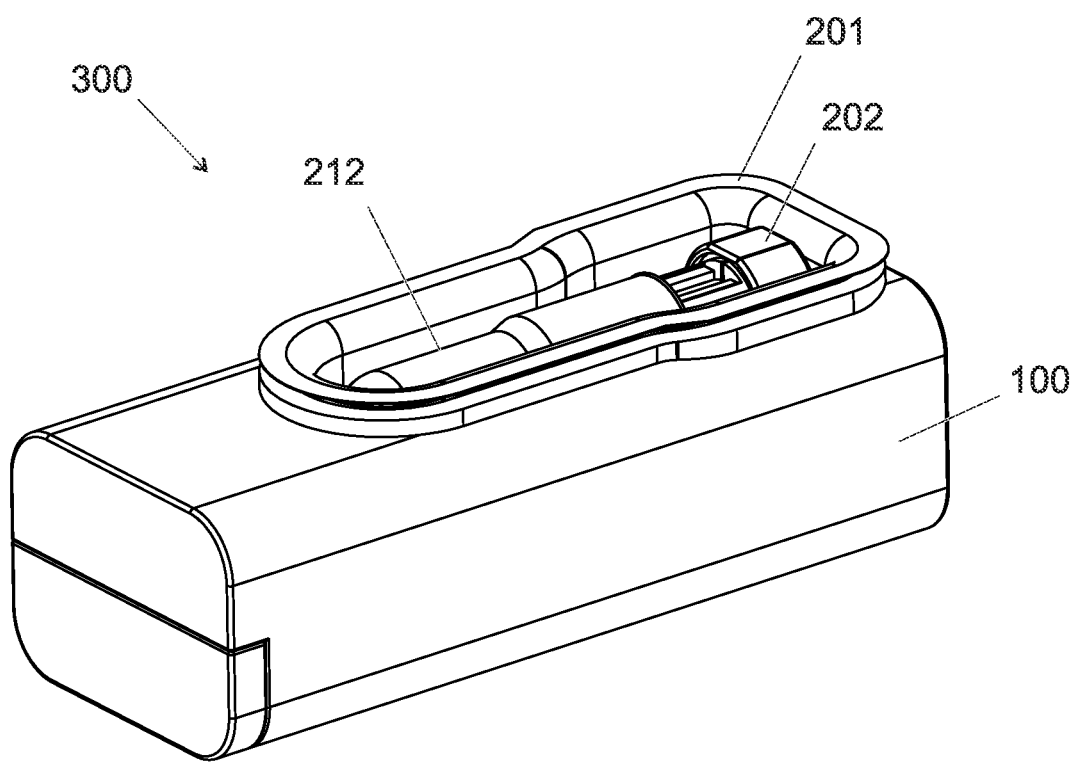
FIG. 4 shows a perspective view of the system of FIGS. 2 and 3, without the lid.

An embodiment of the system 300 without the lid 207 is illustrated in FIG. 4. In this embodiment, the suction pack 201 is (at least partially transparent) so that its content is visible.

As illustrated in FIGS. 5 and 6, then the user (or an operator) activates a vacuum creation mechanism 108 (a piston in this case, comprising a rod 109, which is moved in a direction F3 and then in the opposite direction F4) in the sample extraction device 100 so as to load vacuum into the vacuum chamber 101.

It must be noted that the creation of the vacuum in the vacuum chamber 101 can be performed also before the removing of the lid 207. In another embodiment, the vacuum does not need to be created by a user, e.g. by activating the vacuum creation mechanism 108, but it is already pre-packaged in the system 300 according to the invention. In other words, the system 300 comprises a chamber that is placed under vacuum in the manufacturing assembly line or in a healthcare facility. An example of this embodiment will be discussed with reference to FIG. 36.

Figure 7:
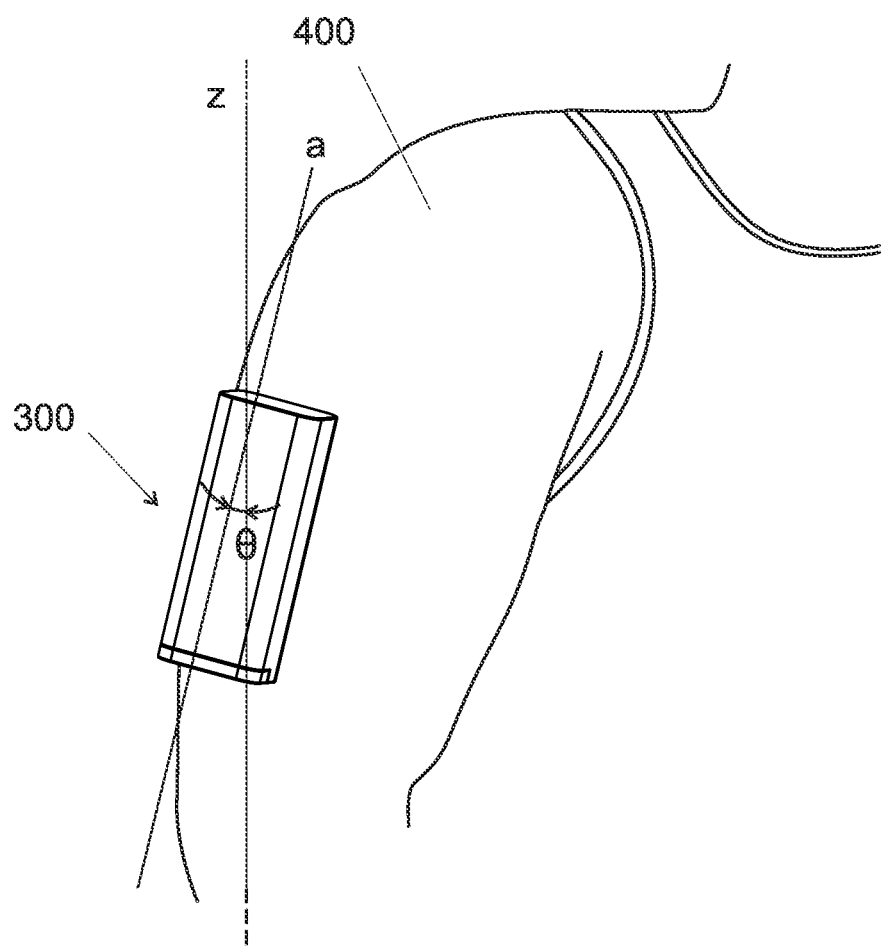
FIG. 7 shows a perspective view of one embodiment of the system according to the invention, placed on an arm of a user.
Figure 14:
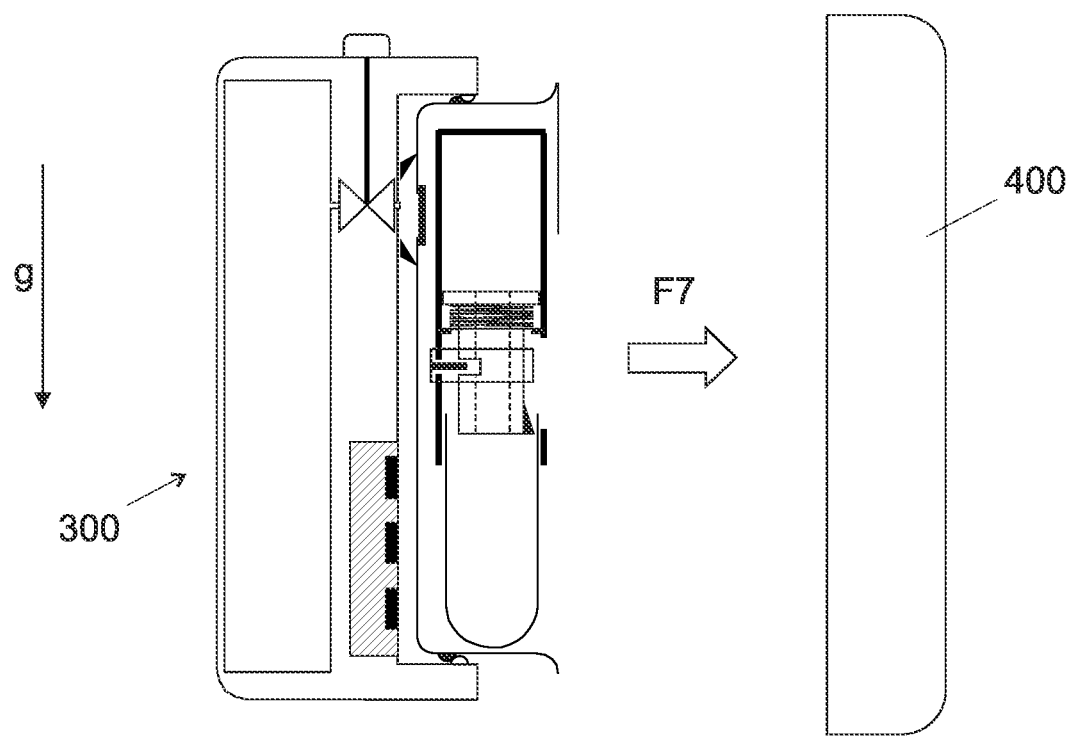
FIG. 14 shows a cross-section view of the embodiment of the system of FIG. 13, approaching a user, e.g. an arm of the user.
Figure 15:
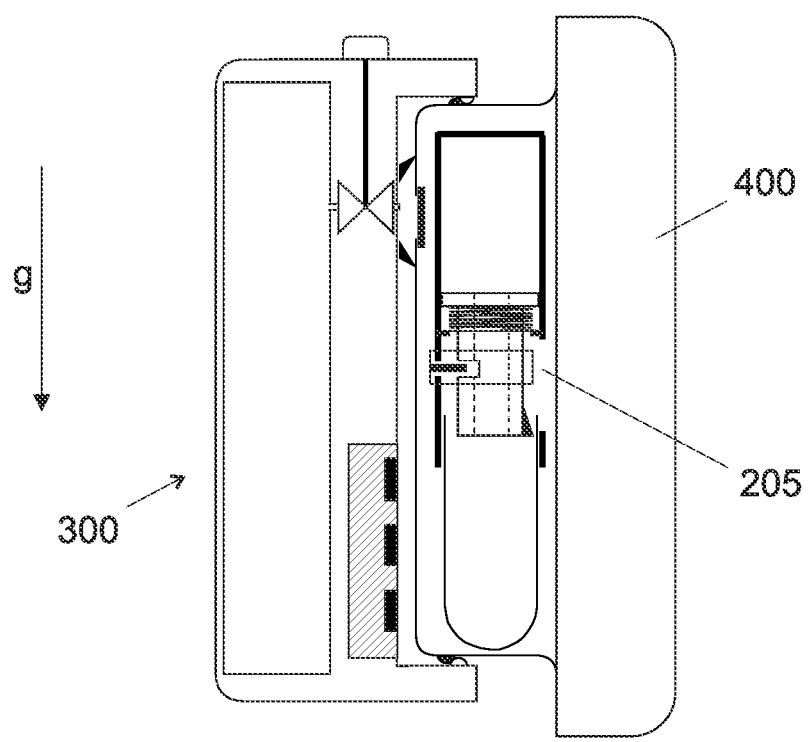
FIG. 15 shows a cross-section view of the embodiment of the system of FIG. 14, wherein the system is placed on the user.

Then, the system 300 approaches the user 400 (as illustrated in FIG. 14) and it is placed on the user 400, as illustrated in FIGS. 7 and 15.

It must be noted that in a preferred embodiment, the system 300 according to the invention is placed on the user arm, in particular an arm kept vertical, in particular with an orientation so that the cap 202 is on top and the bottom of the sample container 212 is at the bottom. However, it could be placed also on other parts of the user (e.g. legs, body, etc.), as long as this part is kept is substantially vertical (i.e. substantially parallel to the direction z of the force of gravity g) or forms a predetermined angle $\theta$ with this direction z. In particular, in a preferred embodiment the angle $\theta$ formed by the direction of the main axis a of the system 300 according to the invention and the direction z of the force of gravity g is comprised in the range 0°-45°. In fact, the system 300 advantageously exploits also the gravity force (in combination with the vacuum) for extracting the desired volume of the fluid sample.

Figure 16:
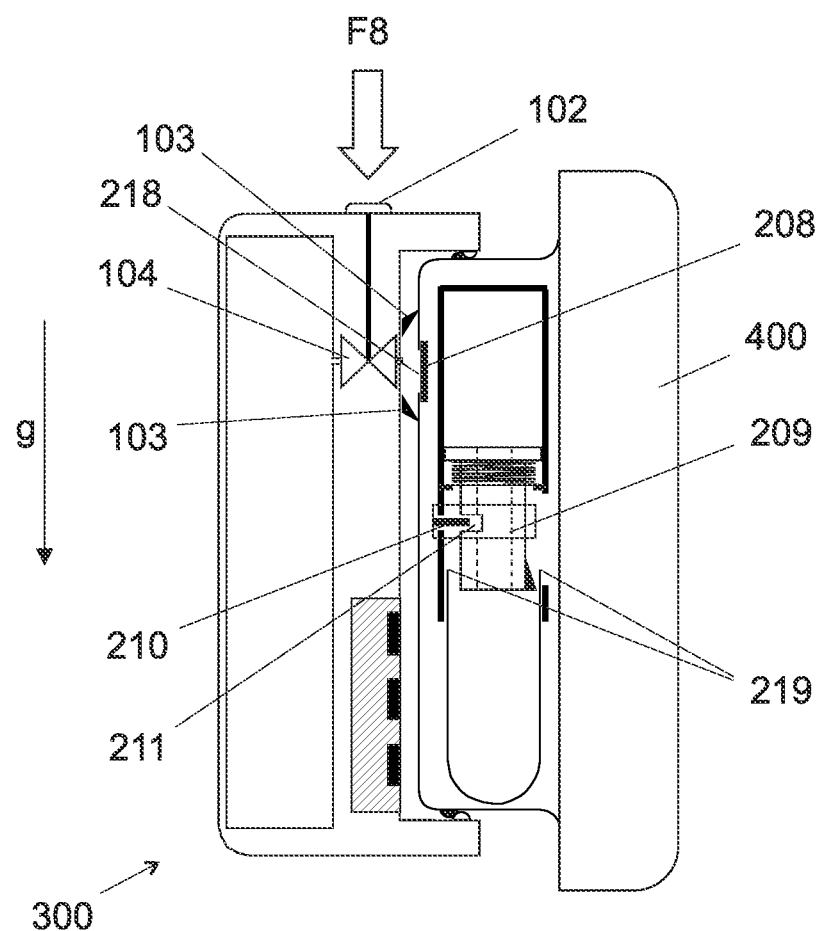
FIG. 16 shows a cross-section view of the embodiment of the system of FIG. 15, wherein the valve control mechanism is activated.

The user (or the operator) actuates then a valve control mechanism 102, which in the example of FIG. 16 is a push-button which is pushed in the direction of the arrow F8. Of course, other kinds of valve control mechanism 102 can be used instead of a push button, e.g. a rotatory button, etc.

The valve control mechanism 102 permits to open the valve 104 so as to transfer the vacuum from the vacuum chamber 101 of the sample extraction device 100 to the suction pack 201.

In a particular embodiment, this transfer is performed through an opening 218 in the suction pack 202, which is covered by a membrane 208 located in the suction pack 202. In one preferred embodiment, the membrane 208 is made of the same material of the lid 207 (e.g. Tyvek®).

This membrane 208 allows also to protect the system 300 from blood contamination that could result in growth of bacteria and cross contamination between patients. In one embodiment, the membrane 208, while letting air go through, prevents bodily fluids like blood permeation.

The vacuum created into the suction pack 201 permits also to maintain the whole system 300 against the skin of the user.

Figure 17:
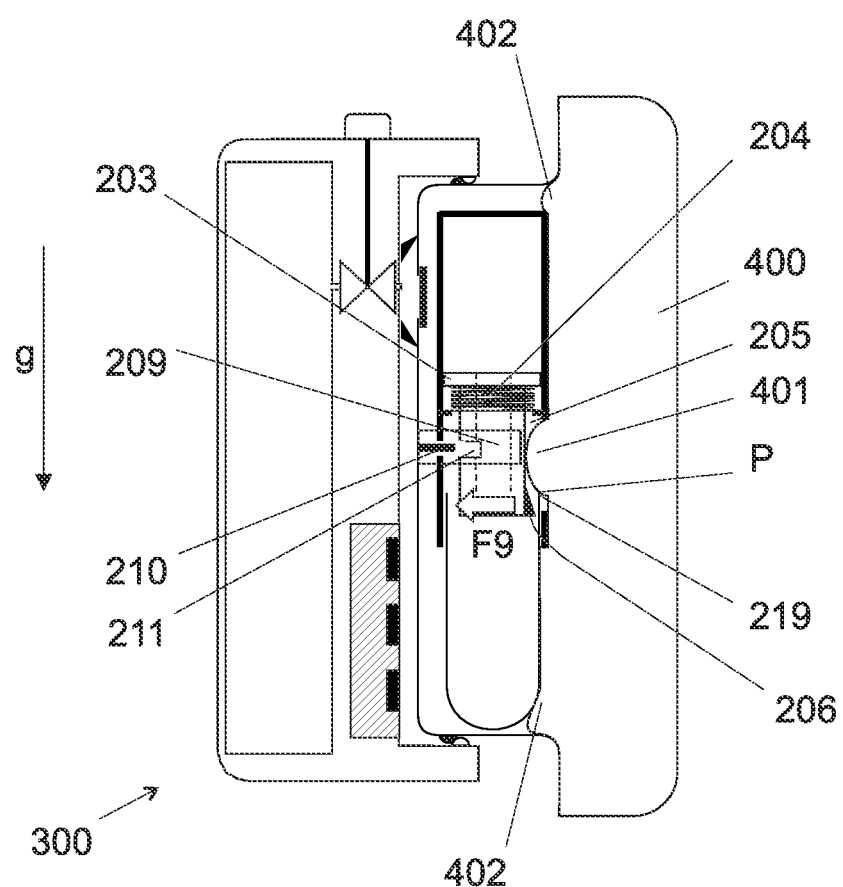
FIG. 17 shows a cross-section view of the embodiment of the system of FIG. 16, wherein the suction created by the vacuum stretches and deforms the user's skin.

It also stretches and/or deforms the user's parts 401 and 402, visible in FIG. 17, among which there is the user's part to be cut 401. The user's part to be cut 401 is the user's part which enter into contact with the collection window 205 of the sample collection device. The user's part to be cut 401, as stretched and/or deformed by the vacuum transferred in the suction pack 201, actuates the triggering mechanism which in turn triggers the incision mechanism.

In fact, as visible in FIG. 17, the stretching and/or the deformation of the skin in the collection window 205 (i.e. the user's part to be cut 401) displaces the triggering element 209, which in the embodiment of FIG. 17 is a half-ring surrounding at least a part of the support element 203 (the piston in FIG. 17), so as to liberate the support element 203.

In fact, the movement of the triggering element 209 in the direction of the arrow F9 in FIG. 17 disengages the finger 210 from the cavity of notch 211 in the triggering element 209.

Figure 18:
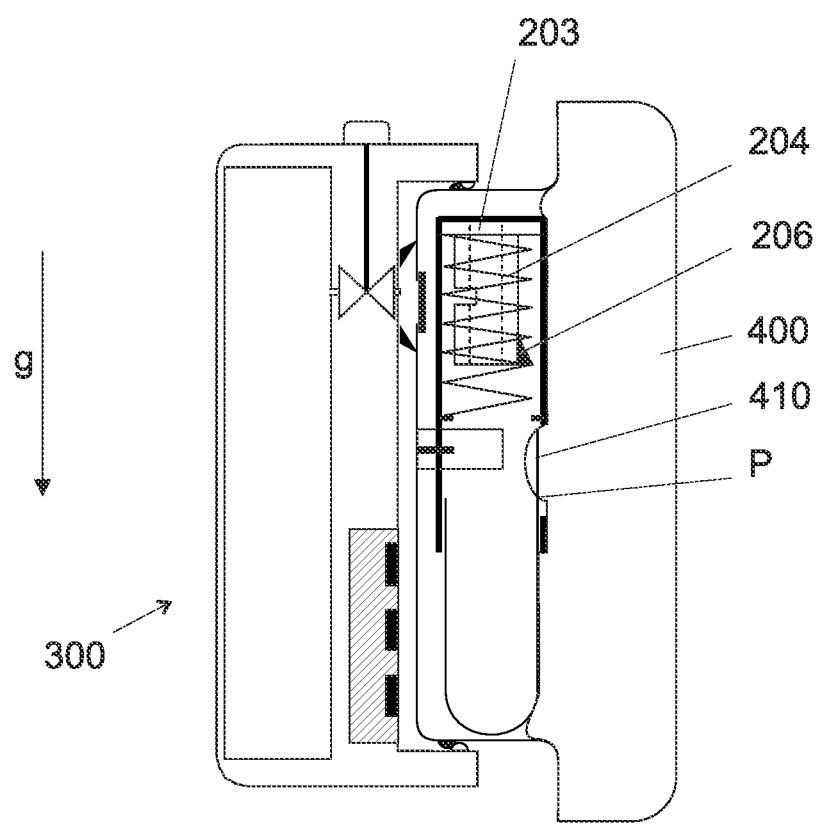
FIG. 18 shows a cross-section view of the embodiment of the system of FIG. 17, wherein the incision mechanism is in the second incision mechanism position and the user's skin has been incised by the incision mechanism.

Therefore, as illustrated in FIG. 18, the loaded elastic element 204 will displace the support element 203 of the incision mechanism inside the cap 202. In other words, the incision mechanism will be moved from a first incision mechanism position in the cap 202 (illustrated e.g. in FIG. 8 or 17) to a second incision mechanism position in the cap 202 (illustrated e.g. in FIG. 9 respectively 18). As the support element 203 of the incision mechanism is connected to the cutting element 206, during this displacement, this cutting element 206 will section a localized part 401 of the stretched and/or deformed skin in the collection window 205.

In other words, the incision is triggered by skin stretching and/or deformation upon applying vacuum in the suction pack 201: no user action is needed to trigger the incision. The system 300 ensures that the skin is sufficiently stretched and/or deformed before triggering the incision mechanism. The skin, when stretched and/or deformed, presses against the triggering element 209 which, when pushed, displaced or deformed, releases the support element 203 onto which the cutting element 206 is connected.

When released, the cutting element 206 moves along the (linear or circular) trajectory of the elastic element 204 it is attached to, and incises the skin on its trajectory.

In the embodiment of FIGS. 8 and 9, advantageously the movement of the incision mechanism from the first incision mechanism position to the second incision mechanism position is a linear movement (i.e. a translation) performed in a direction parallel to a surface of the user to be incised.

The incision into the skin is relatively shallow (less than 5 mm, in particular less than 3 mm into the skin, in length; the depth varies between 1 mm and 2 mm). The cutting element 206 makes a sharp cut into the skin. Moreover, the incision is advantageously made while applying vacuum and/or after vacuum is applied: the skin is deformed and/or stretched and/or pinched into the sample collection device 200 before performing the incision, which reduces the feeling of the pain of the incision.

Figure 19:
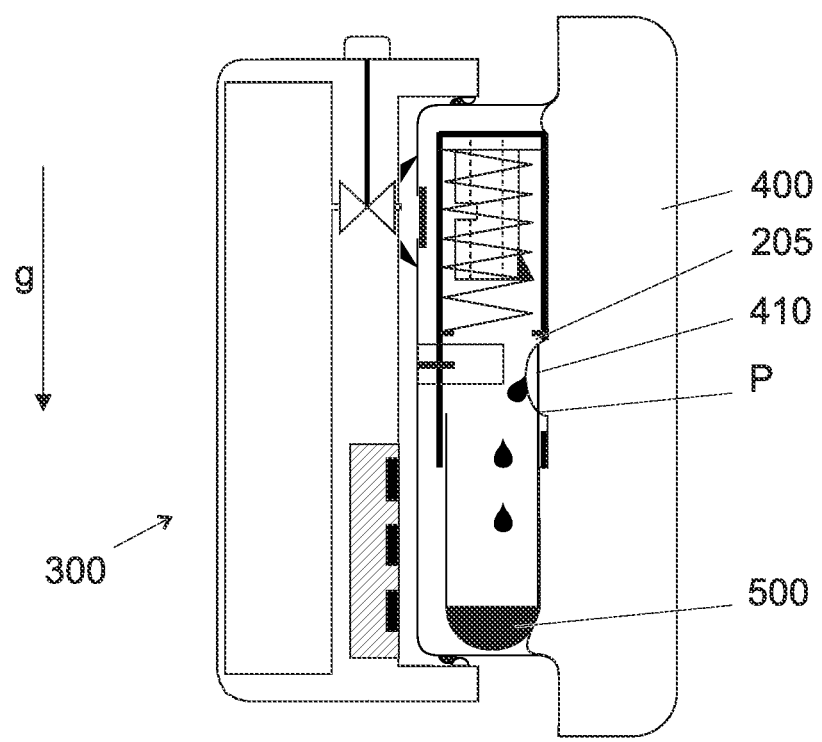
FIG. 19 shows a cross-section view of the embodiment of the system of FIG. 18, wherein the blood is flowing from the incision created by the incision mechanism.
Figure 20:
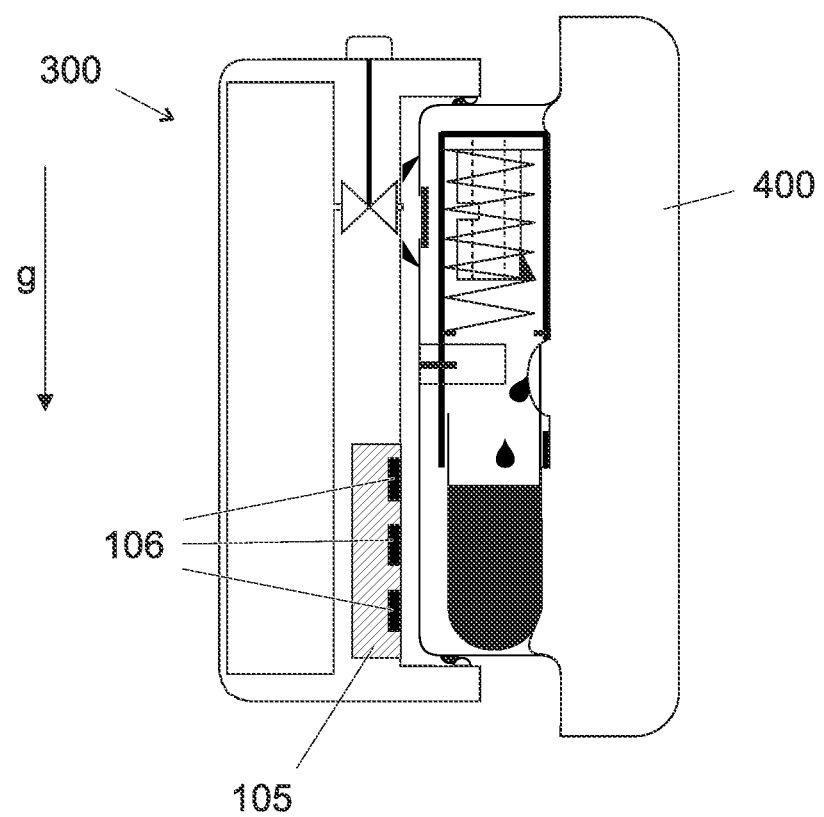
FIG. 20 shows a cross-section view of the embodiment of the system of FIG. 19, wherein according to one embodiment at least one sensor of the system announces the user once the volume of the sample in the sample container has reached a predetermined value.

In one preferred embodiment, illustrated in FIGS. 17 to 19, at least a part of the edge 219 of the sample container 212 is in contact with the user 400 at a contact point or region P, at or under the incision on the user 400 made by the incision mechanism of the system 300. This contact point or region P guarantees that there is no space between the user 400 and the sample container 212, so that the fluid sample can fall down in the sample container 212. In other words, at least a part of the edge 219 is an edge of the collection window.

Advantageously, after the skin incision, the cutting element 206 is retracted into the cap 202, in particular into a cavity 216 visible in FIGS. 8 and 9, with no risk of injury or contamination to anyone handling the sample collection device 200.

In one preferred embodiment, the cutting element 206 is placed at an angle $\alpha$ (illustrated for example in FIG. 34) to maximize the surface cut, without increasing the incision depth. For example, the cutting element 206 can be positioned at a 90° angle with the skin, or it can be placed at a 45° angle with regard to the normal axis of the skin, maximizing the surface of the incision without increasing depth of the incision. In general, the plane containing the cutting element 206 can be positioned anywhere between 45° and 90° with regard to the plane of the skin of the user.

In one embodiment, the length of the trajectory of the cutting element 206 allows to cut more capillaries so as to maximize the blood flow.

The vacuum in the system 300 according to the invention has therefore three main functions:

1) it maintains the system 300 on the user during fluid sample collection;
2) it stretches and/or deforms the skin of the user creating a localized vasodilation of capillaries of the user; and
3) it extracts bodily fluid, e.g. blood from capillaries after the incision has been made.

To guarantee a good sealing between the skin of the user and the suction pack 201, and to maintain vacuum in the suction pack 201, two elements enter into play: first the better the skin stretches and/or deforms into the suction pack 201, the higher is the surface between the skin and the edge of the suction pack 201 and the better the seal is.

In order to favour a good stretching and/or deformation of the skin into the blister, the frictional forces between the skin and the suction pack 201 have to be minimized. This can be done e.g. by the use of the right surface properties of the suction pack 201 and materials inside the suction pack 201 and/or the coating of the suction pack 201 and materials inside the suction pack 201 and/or coating of the skin with a silicone gel, a silicone spray or any other lubricant.

Second, the seal between the skin and the suction pack 201 can be enhanced and better guaranteed if no air can penetrate between the skin and the suction pack 201. In one preferred embodiment, a silicone gel, a silicone spray or any other lubricant placed between the suction pack 201 and the skin can play the role of a sealing agent.

In other words, the materials chosen and the use of a lubricant on the suction pack 201 or on the skin will be used to enhance vacuum.

As illustrated in FIG. 19, the fluid (e.g. the blood) flows from the incision created in the deformation window 205. A sealing edge (illustrated for example in FIGS. 31 and 33, reference number 219') ensures that fluid doesn't flow out of the sample container 212, the edge of the sample container 212 being positioned near the incision 401. The drops of fluid 500 formed at the incision point fall into the sample container 212 by exploiting the gravity force g.

Since the gravity force g, along with the vacuum, are both used for collecting the fluid sample 500, the system 500 according to the invention is designed to collect about 1 ml of fluid sample 500. Moreover, the sample container 212 has a size similar to the tubes used for venepuncture (e.g. diameter 13 mm), making it compatible with known blood analysers.

Figure 21:
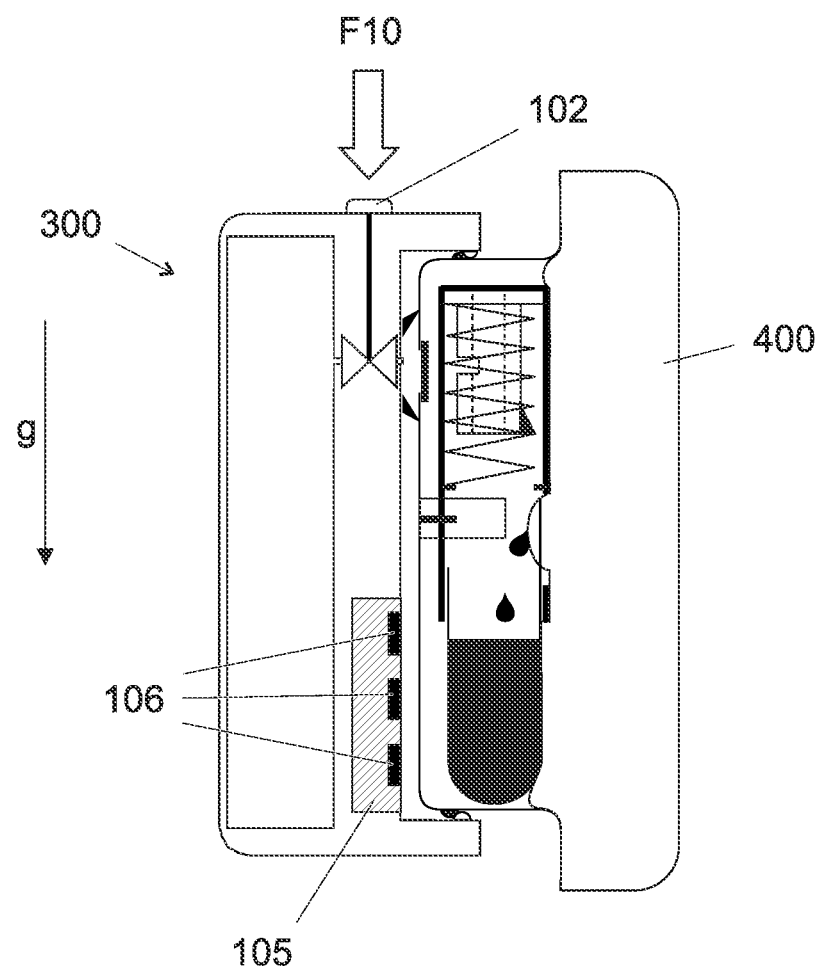
FIG. 21 shows a cross-section view of the embodiment of the system of FIG. 20, wherein according to one embodiment the valve control mechanism is pressed to re-equilibrate the system to atmospheric pressure.

In the embodiment of FIG. 21, the blood extraction device 100 comprises at least a sensor 106, e.g. an optical sensor in correspondence of the closed end 2121 of the sample container 212, so as to detect the fluid sample volume.

In another embodiment (not illustrated), the sensor(s) 106 is/are alternatively or additionally placed on the sample collection device 200.

In one embodiment, once the fluid sample volume has reached a pre-determined value, the system 300 according to the invention indicates to the user (or the operator) the end of fluid sampling, e.g. by a light, a sound or any other appropriate signals.

After a sufficient amount of sample fluid has been collected, In the embodiment of FIG. 21 the user (or the operator) presses the valve control mechanism 102 (or another valve control mechanism) to put back the system 300, and in particular the suction pack 201, at atmospheric pressure.

Figure 22:
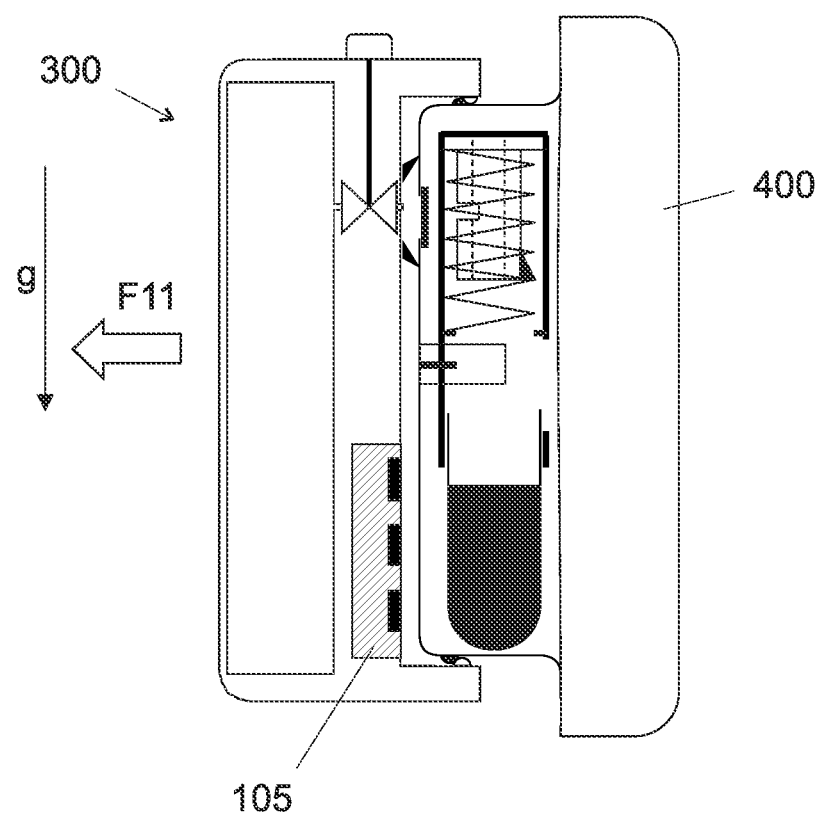
FIG. 22 shows a cross-section view of the embodiment of the system of FIG. 21, wherein the system is removed from the user.

As indicated by the arrow F11 in FIG. 22, the user (or the operator) removes the system 300 from the skin of the user 400.

It is therefore clear that the system 300 according to the invention is arranged to collect a bodily fluid without the need of high-skill training. It could be used by doctors, nurses, non-trained personnel, or by the user (i.e. the patient) himself The system 300 is designed to require minimal action from the user. The system 300 is positioned on the user, preferably on his arm kept vertical, and, pressed against the skin.

The user only actuates the valve control mechanism 102 to generate vacuum. The vacuum stretches and/or deforms the skin into the suction pack 201, maintaining it in place against the user. The user does not need to hold the system 300, he waits for the blood to be collected.

Once the required volume is collected, the user is informed by the system 300 and then actuates again the valve control mechanism 102 to return the system 300 to atmospheric pressure.

In one preferred embodiment, the time for collecting about 1 mL of bodily fluid is in the range of 1 min to 8 min, in particular 5 min.

In one preferred embodiment, the rate with which the fluid, in particular blood, exits from the user once cut by the cutting element 206 of the system 300 is in the range 4 mg/s to 11 mg/s.

Figure 23:
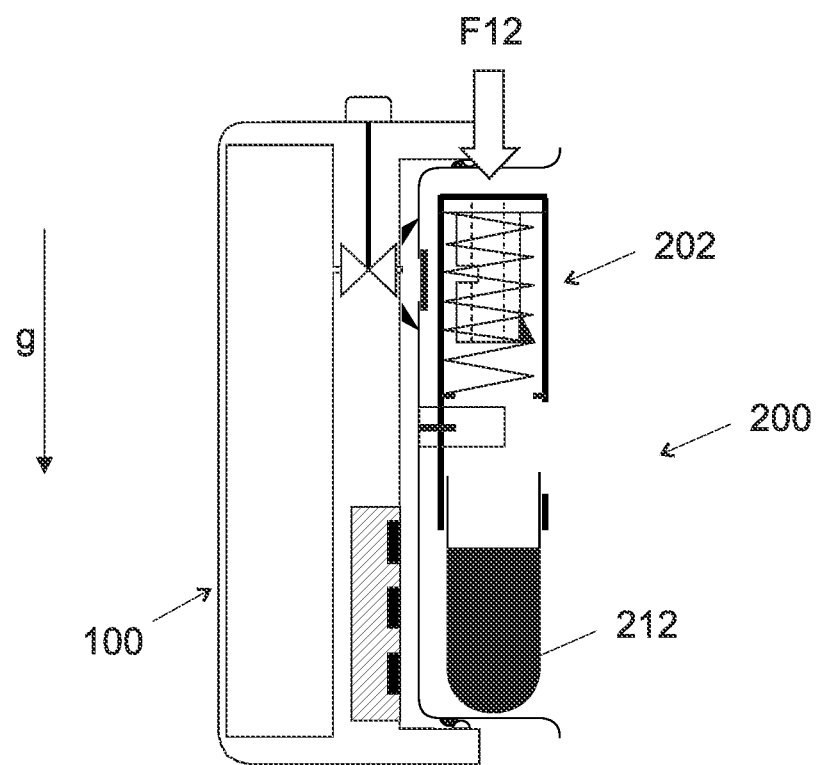
FIG. 23 shows a cross-section view of the embodiment of the system of FIG. 22, wherein the cap is moved to the second cap position.

Then, as illustrated in FIG. 23, the user (or the operator) moves the cap 202 onto the sample container 212 to seal it. In the illustrated embodiment, the cap 202 is moved when it is still in the suction pack 201, to avoid any spillage. In another embodiment, not illustrated, the cap 202 and the sample container 212 are taken out of the suction pack 201 and then the sample container 212 is sealed by the cap 202.

Figure 24:
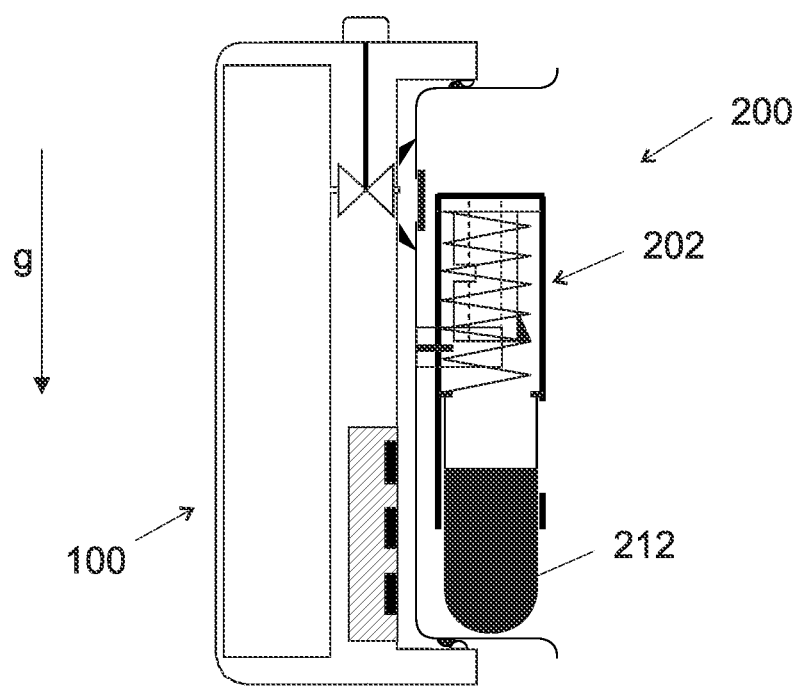
FIG. 24 shows a cross-section view of the embodiment of the system of FIG. 23, wherein the cap is in the second cap position and seals the sample container.

In the embodiment of FIGS. 23-24 (or FIGS. 10A-10B), the movement of the cap 202 from the first cap position to the second cap position is a linear movement, the cap 202 sliding onto (the outer surface of) the sample container 212 during this linear movement, as illustrated by the arrow F12 in FIG. 23.

However, in another embodiment (not illustrated), the movement of the cap from the first cap position to the second cap position is in complement or in alternative a circular movement. For example, the cap 202 can be screwed onto (the outer surface of) the sample container 212.

Figure 25:
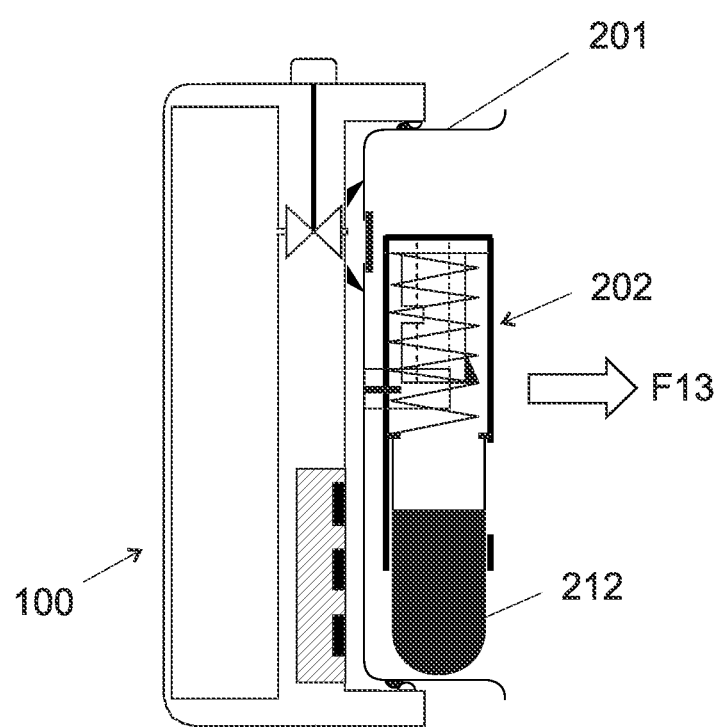
FIG. 25 shows a cross-section view of the embodiment of the system of FIG. 24, wherein the sealed sample container is removed from the suction pack.

As illustrated in FIG. 25, the sealed sample container 212 can be removed from the suction pack 201 and it is ready for transport and for sample analysis.

Figure 26:
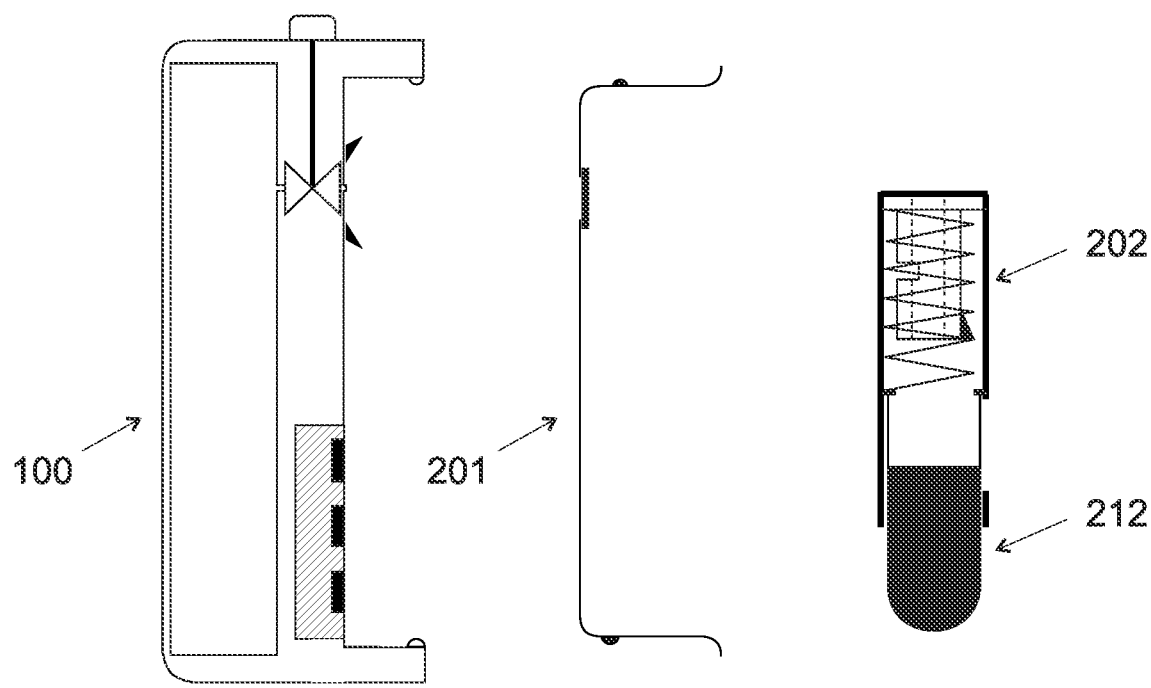
FIG. 26 shows a cross-section view of the embodiment of the system of FIG. 25, wherein the suction pack is removed from the sample extraction device.

As illustrated in FIG. 26, the suction pack 201 can then be removed from the sample extraction device 100.

In another embodiment, not illustrated, the suction pack 201 is first removed from the sample extraction device 100, and them the sample container 212 with the cap 202 are removed from the suction pack 201.

Figure 28:
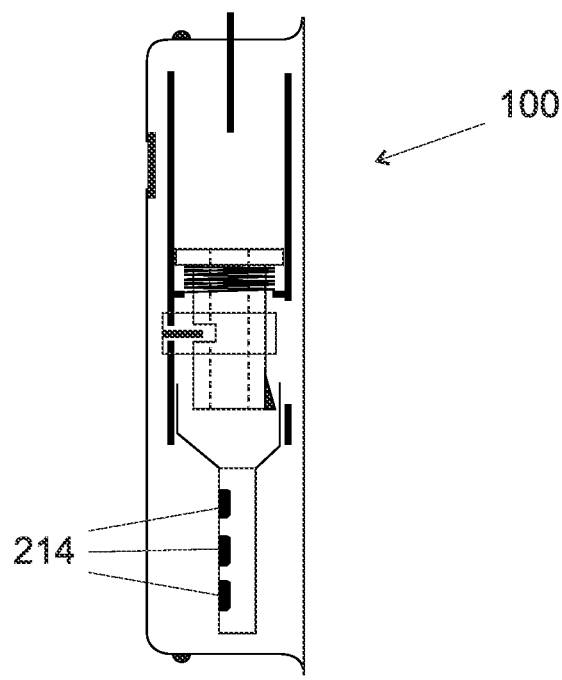
FIG. 28 shows another embodiment of a cross-section view of the sample extraction device.

In the embodiment of FIG. 28, the sample collection device 100 may be used for combining sample collection and testing. In this case, the sample container 212 located in the sample collection device 100 may contain one or several biomarkers pads 214 reacting with the fluid sample, allowing a direct analysis of the fluid sample by the system 300. The chemical reaction will produce a signal, e.g. a visible signal (light, color, etc.) which is proportional to the concentration the target to the measuring in the fluid sample (non exhaustive list: fluorescence, reflectance photometry, etc.). The change in color are captured by the sensor(s) 106 of the sample extraction device and converted into a concentration.

Figure 29:
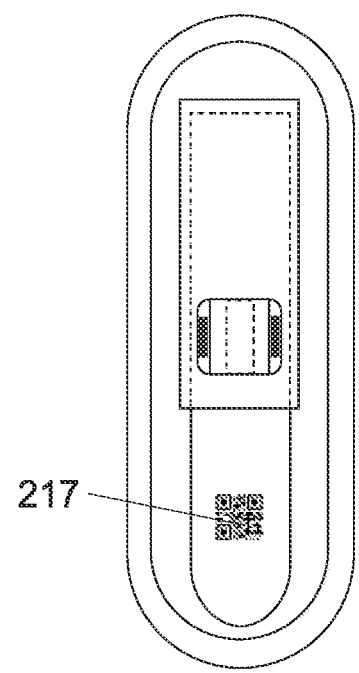
FIG. 29 shows another embodiment of a front view of the sample collection device.

In the embodiment of FIG. 29, the sample extraction device 200, in particular the sample container 212, comprises an ID element 217, e.g. a QR code, a barcode, a number, a RF tag etc.

In another embodiment, the sample extraction device 200 and/or the sample extraction device 100 is (are) arranged so as to store data e.g. blood collection data (such as time of blood collection, level of blood collected, etc.), patient information, sample container barcodes, doctor's prescription data, etc.

In another embodiment, the sample extraction device 200 and/or the sample extraction device 100 is (are) arranged so as to communicate with external devices, in particular portable devices (e.g. smartphones, tablets, etc.) or also to cloud services to which the data can be transferred.

It must be noted that the different features illustrated in the embodiments of FIGS. 1 to 29 (e.g. the trigger element 209 being a half-ring surrounding at least a part of the support element 203, the sample container 212 entering into the cap 202, the linear movement of the incision mechanism, etc.) are not necessarily together present. In other words, different embodiments can be imagined by the skilled person, in which not all the illustrated features are together present.

Figure 30:
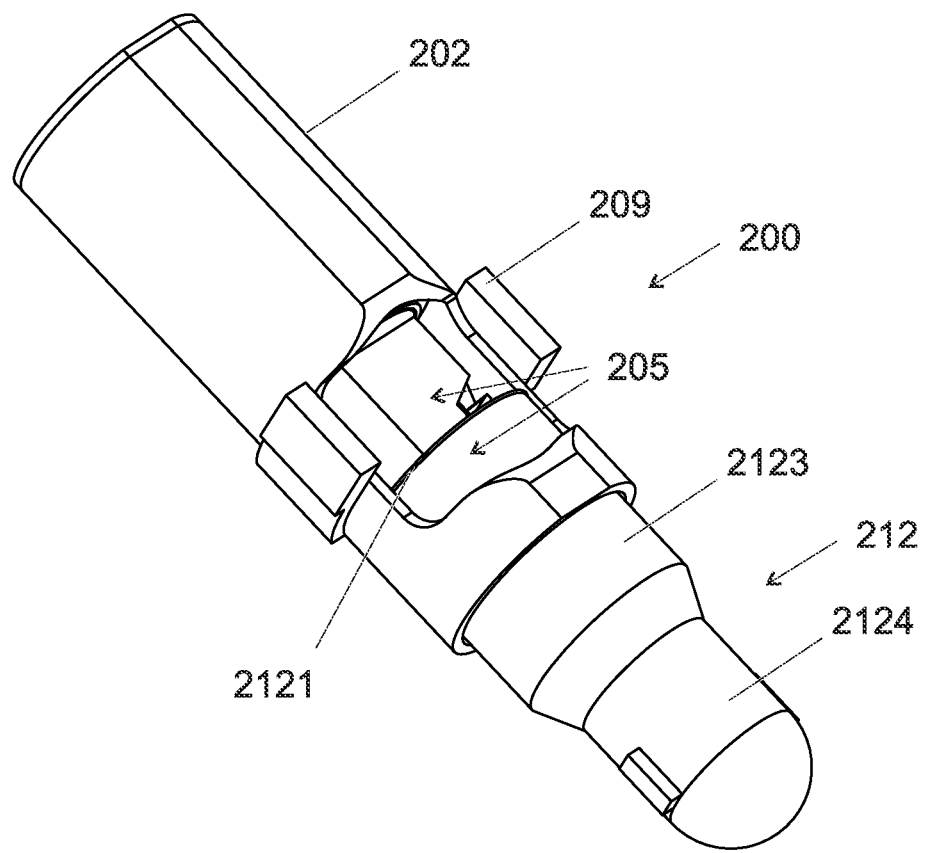
FIG. 30 shows a perspective view of another embodiment of the sample collection device according to the invention.
Figure 31:
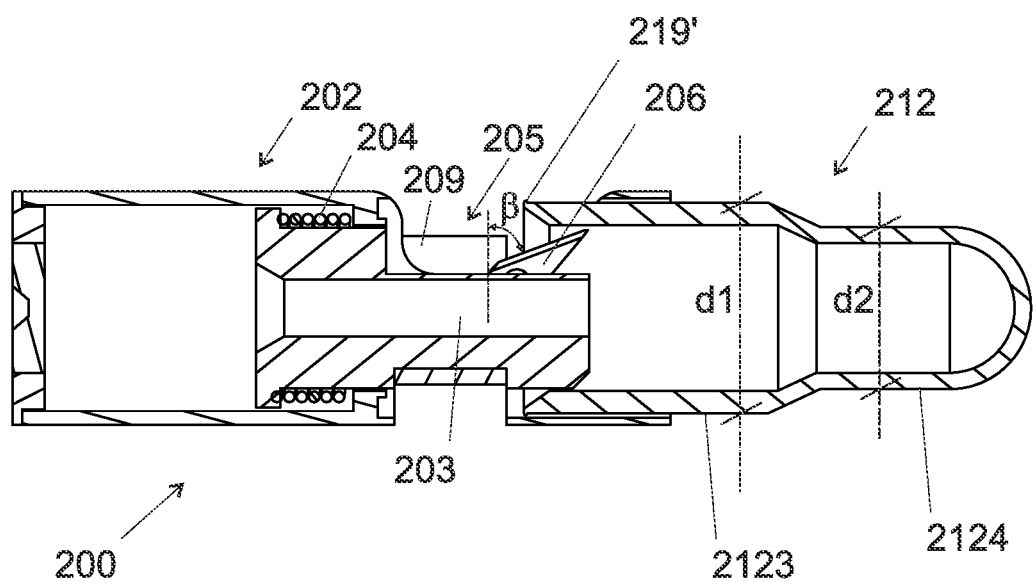
FIG. 31 shows a cross-section view of the embodiment of the sample collection device of FIG. 30.

FIGS. 30 and 31 show a perspective view respectively a cross-section view of another embodiment of the sample collection device 200 according to the invention. In the illustrated embodiment, the trigger element 209 is a demi-ring over the cap 202. In this embodiment, the blade 206 is inclined also of an angle β with regard to the normal axis of the skin (which correspond to the normal axis of the piston 203 when the system 300 is placed on the user's skin), this angle being different from 90°. This allows the cutting element to enter more tangentially into the user's skin. In this embodiment, moreover, the cap 202 is over a part of the sample container 212. In other words, the cap 202 does not enter into the sample container 212, but rather the sample container 212, in particular at least its end 2121, enters into the cap 202. Finally, in this embodiment, the sample container 212 comprises at least two portions 2123, 2124, having different diameters $d_1$ respectively $d_2$. In one particular embodiment, the diameter $d_1$ is a standard diameter according to the definition given above.

It must be noted that the different features illustrated in the embodiment of FIGS. 30, 31 (e.g. the trigger element 209 being a demi-ring over the cap 202, the sample container 212 entering into the cap 202, the sample container 212 comprising two portions 2123, 2124, the inclined blade 206, etc.) are not necessarily together present. In other words, different embodiments can be imagined by the skilled person, in which not all the illustrated features are together present. For example, it is possible imagine a sample collection device 200 in which the trigger element 209 is a demi-ring over the cap 202, the sample container 212 enters into the cap 202, the blade 206 is inclined but the sample container 212 comprises a single portion. Moreover, the embodiment of FIGS. 30, 31 can be combined with any of the other previously or later described embodiments.

Figure 32:
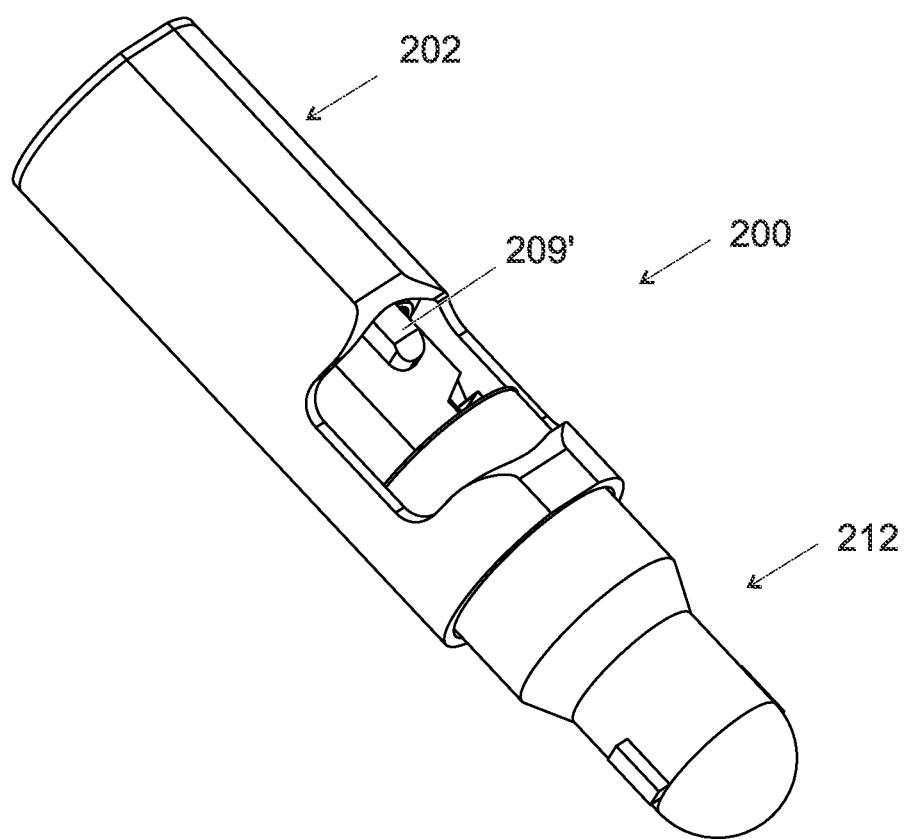
FIG. 32 shows a perspective view of another embodiment of the sample collection device according to the invention.
Figure 33:
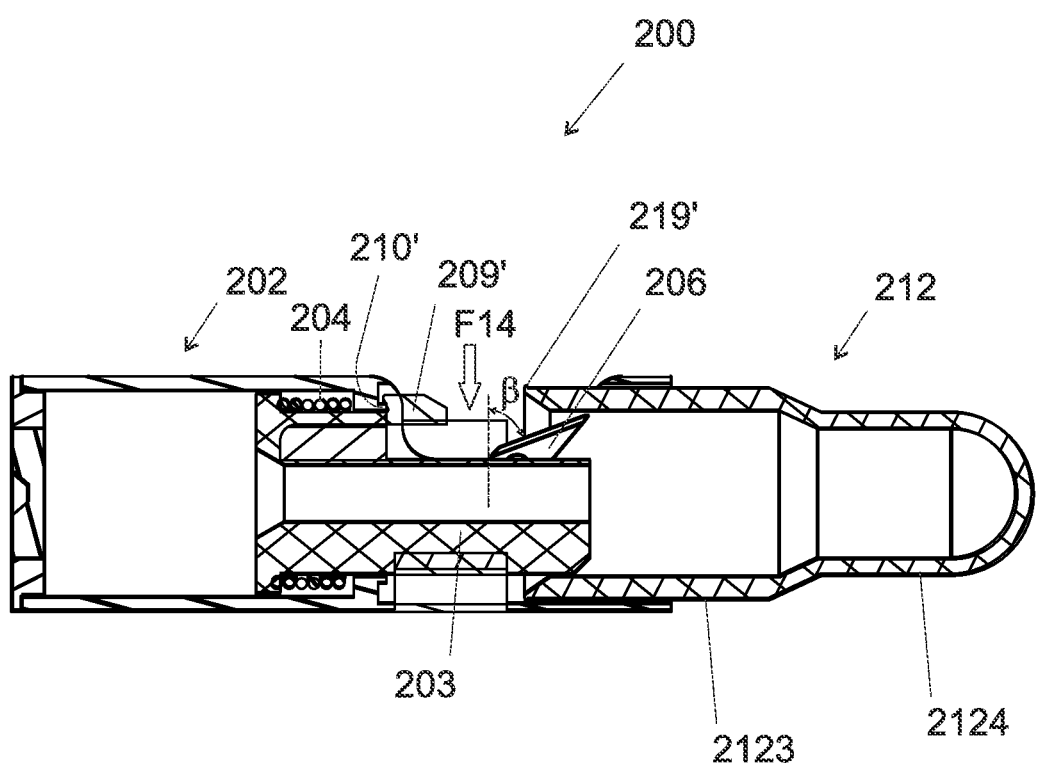
FIG. 33 shows a cross-section view of the embodiment of the sample collection device of FIG. 32.
Figure 34:
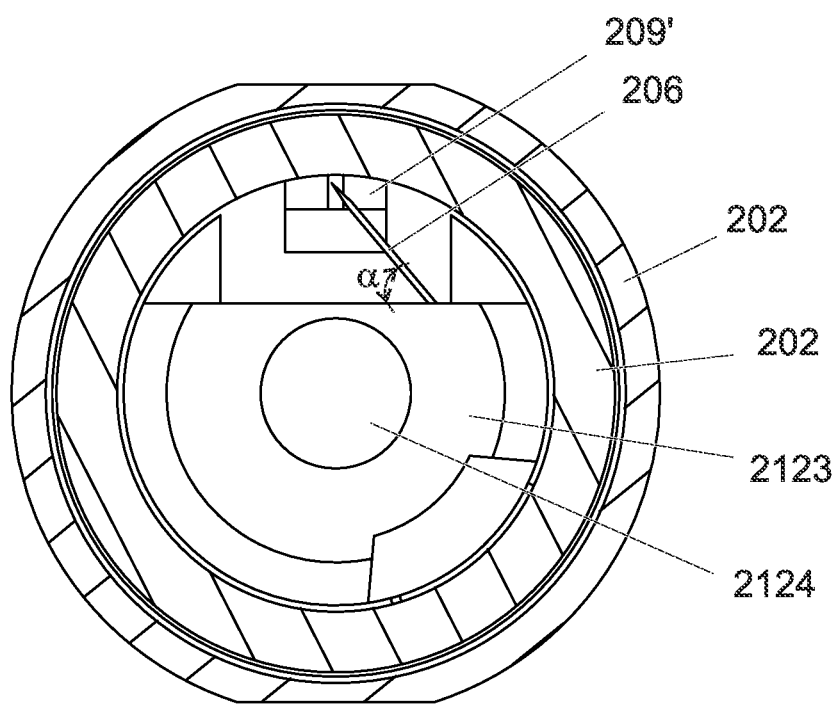
FIG. 34 shows another cross-section view of the embodiment of the sample collection device of FIG. 32.

FIGS. 32, 33 and 34 show a perspective view respectively cross-section views of another embodiment of the sample collection device 100 according to the invention. In the illustrated embodiment, the trigger element 209 is not a demi-ring over the cap 202, as in FIGS. 30 and 31. In this embodiment, the trigger element 209 is a tab 209' in the cap 202, which is held in place by the finger 210'. The skin of the user, once deformed by the vacuum, will move the tab 209' in the direction of the arrow F14, by liberating the tab 209' from the finger 210' so as to liberate the elastic element 204 and therefor the piston 203 with the cutting element 206.

In the embodiment of FIGS. 32, 33 and 34, the blade 206 is inclined of an angle β with regard to the normal axis of the skin, this angle being different from 90°, as in FIGS. 30 and 31. In this embodiment, the cap 202 is over a part of the sample container 212, as in FIGS. 30 and 31. Finally, in this embodiment, the sample container 212 comprises two portions 2123, 2124, having different diameters $d_1$ respectively $d_2$ as in FIGS. 30 and 31. Again, the features illustrated in the embodiment of FIGS. 32, 33 and 34 are not necessarily together present. Moreover, the embodiment of FIGS. 32, 33 can be combined with any of the other previously or later described embodiments.

Figures 35A, 35B:
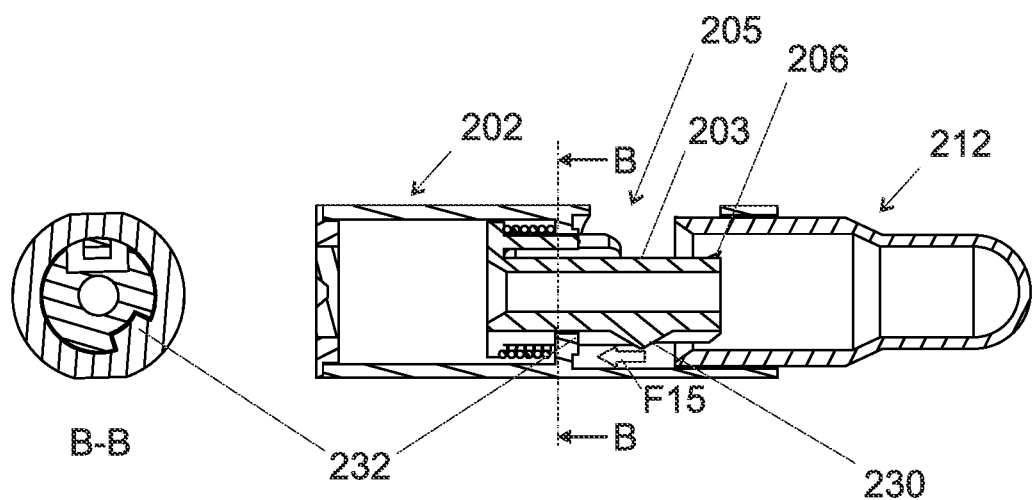
FIG. 35A shows a cross-section view a part of another embodiment of the sample collection device according to the invention.
FIG. 35B shows another cross-section view of the embodiment of the sample collection device of FIG. 35A.

FIGS. 35A and 35B show cross-section views of another embodiment of the sample collection device 200 according to the invention. In this embodiment, the support element 203 comprises a protrusion 230, which, once the support element is moved in the direction of the arrow F15 by the triggering mechanism, will enter into contact with the finger 232 of the cap 202: this will cause a mechanical movement of all the support element 203, and then of the cutting element 206, toward the user's skin, so that the cutting element will move toward the user's skin while cutting it. In such a way, a deeper cut could be realised in the user's skin. The shape and the size of the protrusion 230 and/or of the finger 232 are selected so that the movement of the cutting element 206 toward the user's skin is performed while the cutting element 206 is cutting the user's skin. Other means can be imagined in order to move the cutting element 206 toward the user's skin while it cuts the skin. This embodiment can be combined with any of the other previously or later described embodiments.

Figure 36:
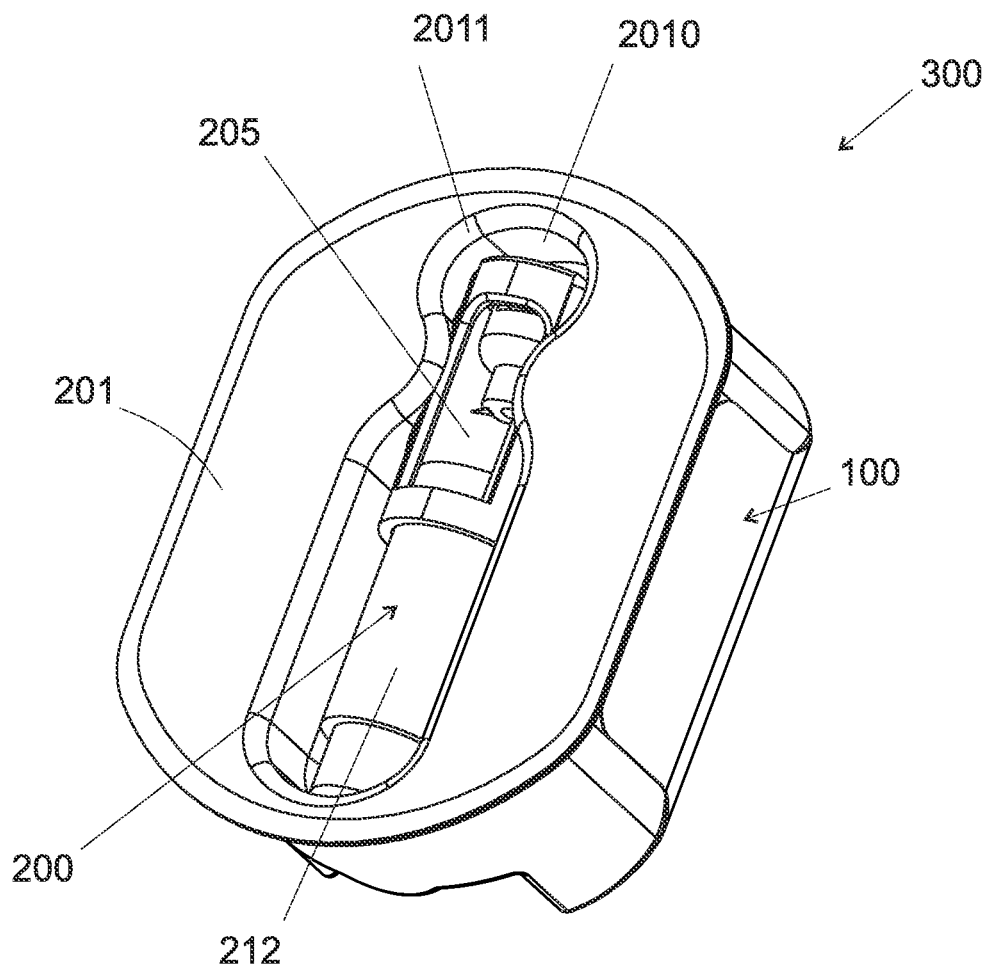
FIG. 36 shows a perspective view of another embodiment of the system for extracting and collecting a sample of a fluid of a user according to the invention.

FIG. 36 shows a perspective view of another embodiment of the system 300 for extracting and collecting a sample of a fluid of a user according to the invention. In this embodiment:
the system 300 is fully consumable;
the vacuum is already pre-packaged in the system 300;
the triggering mechanism is configured so as to perform a circular movement;
the incision mechanism is configured so as to perform a circular movement;
the suction pack comprises an opening which is narrow near or at the collection window;
the lid is not permeable;
the part(s) in contact with the skin is (are) adapted so as to fit to the shape of the user contacting part;
etc.

However, it must be noted that the features illustrated in the embodiments of FIG. 36 are not necessarily together present. In other words, different embodiments can be imagined by the skilled person, in which not all the illustrated features are together present. Moreover, the embodiment of FIG. 36 can be combined with any of the other previously described embodiments.

Figure 37:
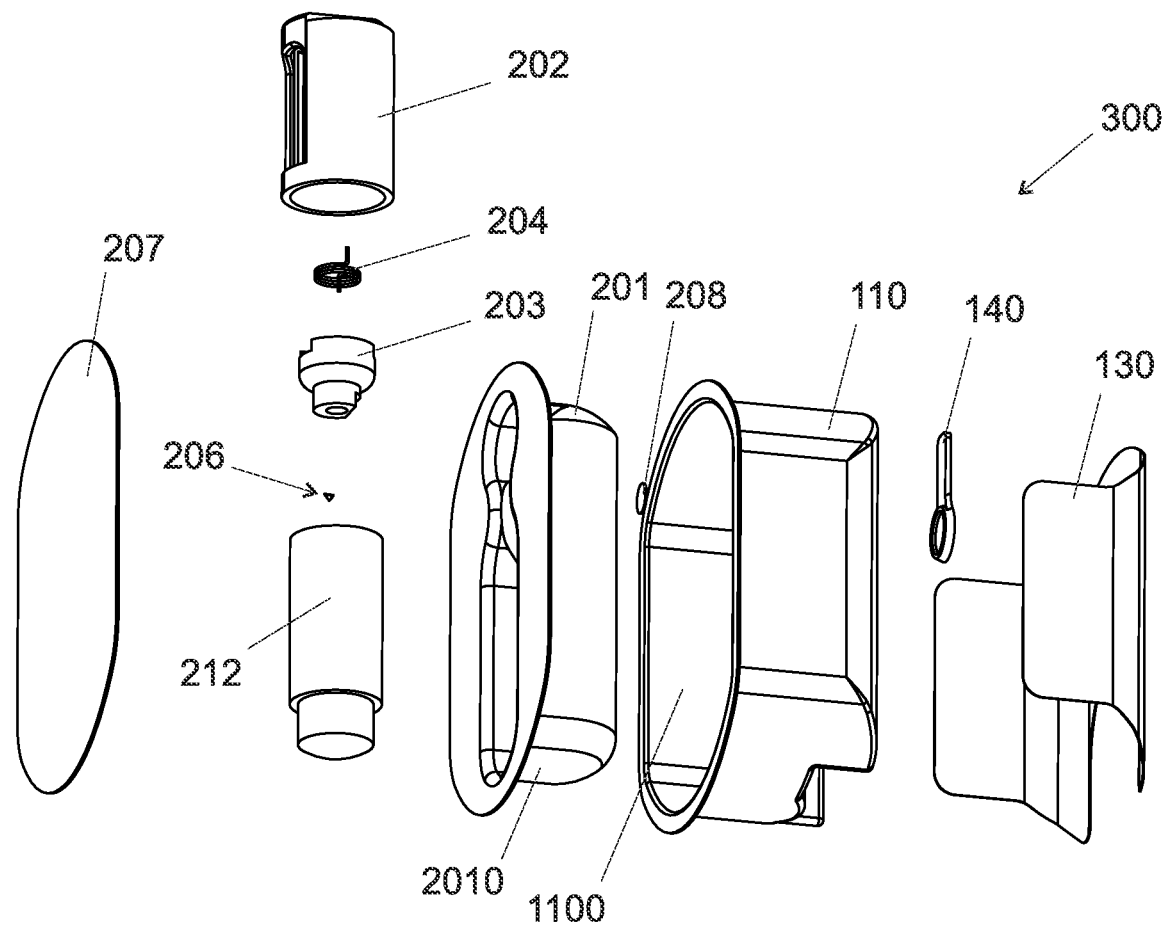
FIG. 37 shows an exploded view of the embodiment of the system of FIG. 36.

FIG. 37 shows an exploded view of the embodiment of the system 300 of FIG. 36. In this figure, the suction pack 201 present in the previously described embodiments is a first suction pack 201 (or inner suction pack 201), and the system 300 comprises a second suction pack 110 (or outer suction pack 110).

The first suction pack 201 comprises a cavity 2010 arranged to receive the sample container 212 and the cap 202, and having a first thickness. The second suction pack 110 comprises a cavity 1100, having a second thickness, which is greater than the first thickness. The first suction pack 201 is arranged to be received by the second suction pack 110, so that the difference between the two thicknesses creates a chamber that is placed under vacuum in the manufacturing assembly line or in a healthcare facility. In other words, the pre-packaged vacuum is made by adding a second suction pack 110 on top of the first suction pack 201 so to create this chamber.

The first and second suction packs are arranged so that, once the second suction pack 110 receives the first suction pack 201, they can be permanently sealed together.

The system 300 of the embodiment of FIG. 37 comprises also means for transferring the vacuum from the chamber placed under vacuum in the manufacturing assembly line or in a healthcare facility (in the following, second vacuum chamber) to the first vacuum chamber 101, once a user wished to activate the system 300.

In one embodiment, the second suction pack 110 comprises a bistable element (as a button) on one of its outer surfaces. An example of such bistable element is visible in FIG. 38, which shows a part of a cross-section view of the embodiment of the system of FIGS. 36, 37.

In this embodiment, the first suction pack 201 comprises also a piercing protrusion (reference 2014 in FIG. 34). Once a user activates the bistable element 2012, e.g. pressing on the second suction pack 110, the piercing protrusion 2014 will pierce a membrane 208 placed on the first suction pack 201, thereby transferring the vacuum in the first vacuum chamber or collection chamber. This will start the collection of the liquid sample. In one preferred embodiment, this membrane is non-permeable, so as to avoid a vacuum transfer before the use of the system 300.

In one embodiment, the second suction pack 110 comprises also one or more holes 2010, completely covered by a removable cap 140, e.g. a rubber removable cap 140. In order to stop the collection of the liquid sample, the user can remove, e.g. by pulling, the removable cap 140 so as to low the pressure in the collection chamber to the atmospheric pressure, thereby stopping the start the collection of the liquid sample.

In the example of FIG. 36, a (removable) label 130 can cover the back of the second suction pack 110.

FIG. 39 shows another part of another cross-section view of the embodiment of the system of FIG. 36. In the illustrated embodiment, the cutting element 206 makes an incision in the skin of the user by moving into a rotational movement around the main central axis of the tube (and cap 202). This rotational movement allows to have a more compact triggering and incision mechanism. In fact, by choosing a rotational movement of the cutting element 206, the overall length of the triggering mechanism is reduced, allowing for a smaller dimension of the cap 202 and a smaller overall system 300.

In one embodiment, the cap 202 comprises on its top one or more deformable elements 2020, visible in FIG. 39, which is(are) arranged to be deformed in the direction of the arrow F16. The deformable element(s) 2020 is(are) part of the triggering mechanism. Upon applying vacuum, the skin is sucked into the chamber and presses against the deformable element(s) 2020 on the cap 202. By pushing the deformable element(s) 2020, the deformable element(s) 2020 free the rotational piston 203 previously loaded with a (torsion) spring 204.

Figures 41A, 41B:
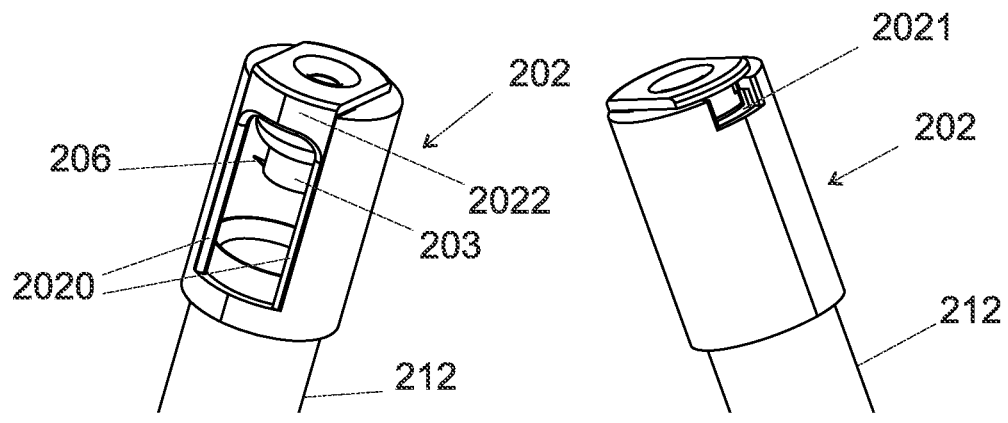
FIG. 41A shows a perspective view (front side) of one embodiment of the sample collection device of the system of FIG. 36.
FIG. 41B shows a perspective view (rear side) of the embodiment of the sample collection device of FIG. 41A.

FIG. 41A shows a perspective view (front side) of one embodiment of the sample collection device of the system of FIG. 36. FIG. 41B shows a perspective view (rear side) of the embodiment of the sample collection device of FIG. 41A. In the illustrated embodiment, the triggering element is part of the cap 202. In another embodiment the deformable elements 2020 belong to a supplementary piece, fixed (in a movable or unmovable way) to the cap 202. The deformable elements 2020 are larger than in previous variants, for a wider area of contact between the skin and the triggering mechanism permitting to have more reliability in the triggering mechanism.

In this embodiment, the cap 202 comprises a liberation notch 2021. When vacuum is released, the skin will press the triggering surface 2022 of the cap 202, by pushing the notch 2021 and setting the piston 203 free.

Increasing the length of the collection window 205, allows to improve the skin stretching. Having a rotational movement of the cutting element 206 allows that the length of the incision is not dependent on the length of the collection window 205 (proportional the window's width), as it is the case with a translational movement of the cutting element 206.

By resuming, having a rotational movement of the cutting element 206 allows the following advantages:
a more compact system 300;
a more reliable triggering mechanism;
a more controlled and defined skin stretching.

In one embodiment, as visible e.g. on FIG. 36, the cavity 2010 of the suction pack 201, arranged to receive the collection container 212, has a waisted shape, which is narrower at or near the collection window 205, in particular at or near the incision area, so as to allow for a better stretching of the skin. The applicant has noticed that the skin deforms well along the edges 2011 of the cavity 2010 of the suction pack 201. To maximize the skin deformation at or near the incision area, the edges of the cavity 2010 of the suction pack 201 are arranged closer to the incision area, by making it narrower.

Figure 42:
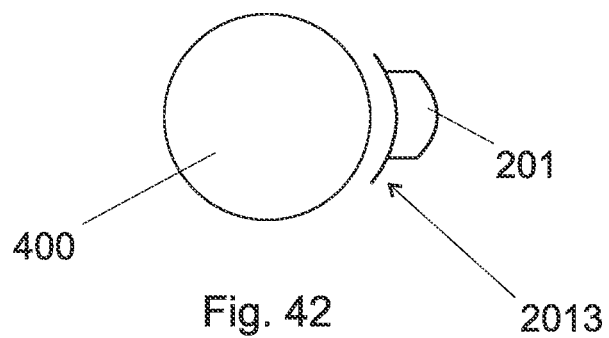
FIG. 42 shows a top view of the system according to the invention, once placed near a user's member, such as an arm.

FIG. 42 shows a top view of the system 300 according to the invention, once placed near a user's member, such as an arm. In this embodiment, the suction pack 201, in contact with the skin, has a shape and/or a curvature 2013 to fit the shape and/or the curvature of the arm 400 to ensure a better seal between the skin and the suction pack 201. In another embodiment (not illustrated), this shape and/or this curvature can be adapted or changed by the user, so as to better fit with the user, in particular with young users.

REFERENCE SIGNS USED IN THE FIGURES

100 Sample extraction device
101 Vacuum chamber
102 Valve control mechanism
103 Gasket
104 Valve
105 Electronic board
106 Sensor
107 Sample collection device port
108 Vacuum creation mechanism
109 Shaft of the vacuum creation mechanism
110 Second suction pack
120 First connection means
130 Label of the second suction pack
140 Cap in the second suction pack
200 Sample collection device
201 Suction pack or first suction pack
202 Cap
203 Support element
204 Elastic element
205 Collection window
206 Cutting element
207 Lid
208 Membrane
209 Trigger element
210 Protrusion (finger)
211 Cavity (interfaced with the finger)
212 Blood collection container
213 Sealing edge
214 Biomarkers pad
215 Open of the cap
216 Cavity in the second cap portion receiving the cutting element
217 ID element
218 Opening in the suction pack
219 Edge
219' Sealing edge
220 Second connection means
230 Protrusion
232 Finger
300 System
400 User's part
401 User's deformed part to be cut
402 User's deformed part
410 Incision
500 Sample
1100 Cavity of the second suction pack
2010 Holes of the second suction pack
2011 Edge of the first suction pack
2012 Bistable element
2013 Curvature of the first suction pack
2014 Piercing protrusion
2010 Cavity of the first suction pack
2020 Deformable element
2021 Notch of the cap
2022 Triggering surface of the cap
2121 Open end of the sample container
2122 Closed end of the sample container
2123 First sample container portion
2124 Second sample container portion
2021 First cap portion
2022 Second cap portion
2120 Open end of the sample container
g Gravity
Fi Arrow (i=1, 2, . . . )
a Main direction of the system 300
θ Angle between the vertical direction (gravity direction) and the main direction of the system 300
α First angle of the cutting element
β Second angle of the cutting element
P Contact point or region
d1 Diameter of the first sample container portion
d2 Diameter of the second sample container portion

The invention claimed is:

1. A sample collection device for collecting a sample of blood, including capillary blood, of a user, the sample collection device comprising:
a sample container arranged to receive said sample and comprising an open end;
a cap arranged to cooperate with said sample container so as to close said open end, said cap being arranged to be moved in and/or on the sample container from a first cap position to a second cap position, wherein in the first and in the second cap positions said cap is at least partially in contact with said sample container so as to guide the movement of the cap from the first cap position to the second cap position, said cap comprising:
a collection window arranged to enter into contact with an area of the user to be incised; and
a cutting system comprising a blade, a support element and a triggering mechanism, wherein the triggering mechanism is configured to move between a first triggering element position and second triggering element position, wherein the triggering mechanism in the first triggering element position holds the support element in a fixed position, wherein the blade is directly connected to the support element movable in the cap by activation of the triggering mechanism to the second triggering element position causing movement of the support element and the blade from a first blade position to a second blade position, wherein during said moving the blade is arranged to incise at the collection window the area of the user so as to exit the sample from the user, said sample exiting the user and entering said sample container, and wherein during the moving from the first blade position to the second blade position the cap is in the first cap position;
wherein the cap comprises a first cap portion and a second cap portion, wherein the second cap portion is configured to seal said sample container when the cap is in the second cap position, so as to safely transport said sample.

2. The sample collection device of claim 1, wherein the first cap portion comprises the collection window arranged to enter into contact with the user.

3. The sample collection device of claim 2, wherein the second cap portion comprises a cavity for receiving the blade once it is in said second blade position, so that the blade is irreversibly and safely retracted in the cavity so that it can no longer incise the user.

4. The sample collection device of claim 1, wherein
the support element is a piston comprising the blade; and
a spring is blocked in a compressed position by the triggering mechanism, said spring, once the blade is triggered, being free to be decompressed, said decompression moving the piston and then the blade from the first blade position to the second blade position.

5. The sample collection device of claim 4, wherein the cap includes a finger and the piston comprises a protrusion cooperating with the finger so that the movement of the blade from the first blade position to the second blade position is toward the user's skin while the blade cuts the skin.

6. The sample collection device of claim 4, wherein a finger is arranged to be moved from a first triggering element position, and wherein it holds the spring in a blocked position and the piston in a fixed position, to a second triggering element position wherein the finger no longer holds the spring nor the piston.

7. The sample collection device of claim 1, further comprising a suction pack arranged to receive the sample container and the cap, the suction pack comprising a membrane allowing a vacuum to enter in the suction pack.

8. The sample collection device of claim 1, said sample container being a tube, the tube being arranged to be entered in a blood analysis apparatus.

9. A system for extracting and collecting a sample of blood, especially capillary blood, of a user, comprising:
the sample collection device according to claim 1;
a sample extraction device, comprising:
a port arranged to receive at least a part of said sample collection device;
a vacuum chamber;
a vacuum piston and rod arranged to create a vacuum in the vacuum chamber;
a valve arranged to close and/or open the vacuum chamber, and/or to release the sample collection device to atmospheric pressure;
a button arranged to command the valve so as to release the vacuum from the vacuum chamber to the sample collection device, and/or to release the sample collection device to atmospheric pressure.

10. The system of claim 9, wherein the sample extraction device comprises an electronic module comprising a power supply.

11. The system of claim 9, wherein the sample extraction device comprises at least a sensor for detecting a predetermined sample volume in the sample container.

12. The system of claim 9, wherein the sample extraction device comprises an alerting mechanism, indicating to the user the end of the sample extraction by an audio and/or visible signal.

13. The system of claim 9, wherein the sample extraction device comprises a gasket cooperating with an area of the sample collection device comprises a membrane.

14. The system of claim 9, wherein the sample collection device and the sample extraction device form a single consumable system.

15. A method for extracting and collecting a sample of, blood, including capillary blood, of a user by using the system according to claim 9, comprising the following steps:
packaging the sample collection device into a suction pack;
placing the suction pack containing the sample collection device on or in the sample extraction device to form a combined system;
placing the combined system on an area of the user to be incised, so that the collection window enters into contact with said area of the user to be incised, wherein said area of the user to be incised is kept substantially vertical, or the angle (θ) formed by the direction (a) of the main axis of the combined system and the direction (z) of the force of gravity (g) is comprised in the range 0°-45°;
actuating the button, so as to open the valve so as to transfer the vacuum from the vacuum chamber of the sample extraction device to the suction pack of the sample collection device through an opening in the suction pack, said opening being covered by a membrane located in the suction pack;
stretching and/or deforming the user's skin in the area to be incised by the vacuum in the suction pack;
actuating, by the stretched and/or deformed user's skin in the area to be incised the finger which in turn triggers the blade;
moving the blade from the first blade position in the cap to the second blade position in the cap so that the blade sections the stretched and deformed skin of the user;
collecting a volume of blood sample in the sample container;
moving the cap onto the sample container from the first cap position to the second cap position to seal the sample container.

16. The method of claim 15, further comprising:
after the skin incision, retracting the blade into the cap, with no risk of injury or contamination to anyone handling the sample collection device.

17. The method of claim 15, wherein packaging the sample collection device in the suction pack comprises:
placing the cap in and/or on the sample container, said cap being at least partially in contact with said sample container;
packaging the sample container and the cap in the suction pack;
closing the suction pack by a lid;
sterilizing the closed suction pack;
placing the sterilized suction pack on or in the sample extraction device.

18. The method of claim 15, further comprising:
mechanically connecting the sterilized suction pack to the sample extraction device;
removing the lid of the suction pack;
activating the vacuum piston and rod of the sample extraction device so as to load vacuum into the vacuum chamber.

19. The method of claim 15, further comprising:
once the blood sample volume has reached a pre-determined value, indicating to the user the end of blood sampling;
pressing the button to put back the system, and in particular the suction pack, at atmospheric pressure.

20. The method of claim 15, further comprising:
removing the system from the skin of the user;
removing the sealed sample container from the suction pack;
removing the suction pack from the sample extraction device.

\* \* \* \* \*